United States Patent
Borrero et al.

(10) Patent No.: US 10,973,706 B2
(45) Date of Patent: Apr. 13, 2021

(54) MULTI-CORE ABSORBENT ARTICLE

(71) Applicant: Drylock Technologies NV, Zele (BE)

(72) Inventors: Ricardo Borrero, Altoona, WI (US); Michael Wayne Harris, Eau Claire, WI (US)

(73) Assignee: Drylock Technologies NV, Zele (BE)

( * ) Notice: Subject to any disclaimer, the term of this patent is extended or adjusted under 35 U.S.C. 154(b) by 847 days.

(21) Appl. No.: 15/542,266

(22) PCT Filed: Jan. 8, 2016

(86) PCT No.: PCT/US2016/012710
§ 371 (c)(1),
(2) Date: Jul. 7, 2017

(87) PCT Pub. No.: WO2016/112328
PCT Pub. Date: Jul. 14, 2016

(65) Prior Publication Data
US 2017/0367905 A1    Dec. 28, 2017

Related U.S. Application Data

(60) Provisional application No. 62/101,469, filed on Jan. 9, 2015.

(51) Int. Cl.
*A61F 13/535* (2006.01)
*A61F 13/531* (2006.01)
*A61F 13/84* (2006.01)

(52) U.S. Cl.
CPC .... *A61F 13/535* (2013.01); *A61F 2013/5317* (2013.01); *A61F 2013/8402* (2013.01)

(58) Field of Classification Search
CPC ............ A61F 13/535; A61F 2013/5355; A61F 2013/5317; A61F 2013/8402
See application file for complete search history.

(56) References Cited

U.S. PATENT DOCUMENTS

| 4,895,568 A | 1/1990 | Enloe |
| 4,994,037 A * | 2/1991 | Bernardin ......... A61F 13/15203 604/368 |

(Continued)

FOREIGN PATENT DOCUMENTS

| EP | 2246017 A1 | 11/2010 |
| WO | WO-2015002934 A2 | 1/2015 |
| WO | WO-2016112328 A1 | 7/2016 |

OTHER PUBLICATIONS

"International Application Serial No. PCT/US2016/012710, International Preliminary Report on Patentability dated Jul. 20, 2017", 8 pgs.

(Continued)

*Primary Examiner* — Michele M Kidwell
(74) *Attorney, Agent, or Firm* — Schwegman Lundberg & Woessner, P.A.

(57) ABSTRACT

An absorbent article such as a diaper can include three or more absorbent core structures for improved acquisition speed, reduced bulkiness, increased retention capacity, and improved dryness, including over multiple insults. The three or more absorbent core structures can at least partially overlap in a stacked or layered configuration in an insult zone of the article. At least one of the core structures can include an absorbent polymer or airlaid material. The absorbent polymer can be located primarily in the insult zone, and one or more of the absorbent core structures can extend beyond the insult zone. In an example, each of the at least three absorbent core structures has a different body-side surface area.

22 Claims, 16 Drawing Sheets

(56) References Cited

U.S. PATENT DOCUMENTS

| | | | | |
|---|---|---|---|---|
| 5,387,208 A | * | 2/1995 | Ashton | A61F 13/531 |
| | | | | 604/358 |
| 5,562,646 A | * | 10/1996 | Goldman | A61L 15/42 |
| | | | | 604/368 |
| 5,591,149 A | * | 1/1997 | Cree | A61F 13/47218 |
| | | | | 604/368 |
| 6,066,775 A | | 5/2000 | Bachar | |
| 6,221,460 B1 | * | 4/2001 | Weber | A61F 13/4942 |
| | | | | 428/131 |
| 6,486,754 B1 | * | 11/2002 | Hidaka | H01P 1/20381 |
| | | | | 333/219 |
| 7,090,667 B2 | * | 8/2006 | Fell | A61F 13/53418 |
| | | | | 604/398 |
| D802,754 S | * | 11/2017 | Borrero | D24/126 |
| 2003/0125698 A1 | | 7/2003 | Ruman et al. | |
| 2003/0144641 A1 | * | 7/2003 | Chen | A61F 13/535 |
| | | | | 604/368 |
| 2003/0208176 A1 | | 11/2003 | Waksmundzki et al. | |
| 2006/0178650 A1 | * | 8/2006 | Hakansson | A61F 13/53717 |
| | | | | 604/378 |
| 2015/0133884 A1 | * | 5/2015 | Hao | A61F 13/535 |
| | | | | 604/378 |
| 2016/0136013 A1 | * | 5/2016 | Peri | A61F 13/537 |
| | | | | 604/385.101 |
| 2019/0076304 A1 | * | 3/2019 | Borrero | A61F 13/49019 |
| 2019/0307616 A1 | * | 10/2019 | Glaug | A61F 13/5638 |

OTHER PUBLICATIONS

"International Application Serial No. PCT/US2016/012710, International Search Report dated Jun. 3, 2016", 4 pgs.

"International Application Serial No. PCT/US2016/012710, Written Opinion dated Jun. 3, 2016", 6 pgs.

"European Application Serial No. 16735500.7, Extended European Search Report dated Jun. 6, 2018", 8 pgs.

* cited by examiner

| MEAN RATE OF ACQUISITION, SECOND INSULT (SECONDS) | |
|---|---|
| ARTICLE L-1 | 41.26 |
| ARTICLE L-2 | 46.26 |
| ARTICLE L-3 | 45.67 |
| ARTICLE L-4 | 39.20 |
| ARTICLE L-5 | 39.07 |
| ARTICLE L-6 | 62.51 |
| ARTICLE L-7 | 58.51 |
| ARTICLE L-8 | 47.37 |
| ARTICLE L-9 | 39.30 |
| ARTICLE L-10 | 38.62 |
| ARTICLE L-11 | 38.97 |

| MEAN RATE OF ACQUISITION, THIRD INSULT (SECONDS) | |
|---|---|
| ARTICLE L-1 | 44.28 |
| ARTICLE L-2 | 48.33 |
| ARTICLE L-5 | 43.92 |
| ARTICLE L-6 | 68.61 |
| ARTICLE L-7 | 62.04 |
| ARTICLE L-8 | 49.82 |
| ARTICLE L-9 | 40.37 |

| MEAN RETENTION CAPACITY (GRAMS) | |
|---|---|
| ARTICLE L-1 | 785.65 |
| ARTICLE L-2 | 1214.52 |
| ARTICLE L-3 | 1046.36 |
| ARTICLE L-4 | 782.24 |
| ARTICLE L-5 | 818.84 |
| ARTICLE L-6 | 921.07 |
| ARTICLE L-7 | 913.63 |
| ARTICLE L-8 | 660.77 |
| ARTICLE L-9 | 695.91 |
| ARTICLE L-11 | 703.94 |

MULTI-CORE ABSORBENT ARTICLE

RELATED APPLICATIONS

This application is a national stage entry of PCT/US2016/012710 with an International Filing Date of Jan. 8, 2016, which claims the benefit of and priority to U.S. Provisional Patent Application Ser. No. 62/101,469, filed Jan. 9, 2015, the contents of each of which are hereby incorporated by reference herein in their entireties.

BACKGROUND

An incontinent adult, child, or infant can use an absorbent article, such as a diaper, that is capable of absorbing or containing human waste products. Diapers can have various shapes and sizes, and are generally configured to be worn between an individual's legs and secured about the waist. Some diapers are reusable and include a washable woven cloth material that can be worn in combination with a fluid-impervious outer garment. Some diapers are disposable and are intended to be discarded after a single use. Such diapers can be configured with a fluid-impermeable or fluid-impervious outer layer (back sheet) and an absorbent inner portion (core).

Some diapers are configured like traditional cloth underwear products and include an elastic waistband instead of, or in addition to, one or more fasteners. Such underwear or brief-style diapers can have front and back panels that are permanently joined together at the sides or hips of the wearer. In an example, the front and back panels can be coupled using an ultrasonic weld that fuses the side edges together. Such diapers are configured to be drawn up over the wearer's legs when the wearer puts on the diaper. These diapers can include absorbent members that are positioned between the wearer's legs and are configured to absorb body fluids.

Some absorbent articles for the incontinence market, such as overnight briefs, are configured for extended wear and high absorbency. In some examples, incontinent individuals can wear the same absorbent article for twelve hours or more. Such high-absorbency products are generally large or oversized, and can be heavy compared to a daytime or regular absorbency article. A high absorbency article can weigh about 150 grams, and its absorbent core can include a relatively large amount of super-absorbent polymer (SAP).

OVERVIEW

The present inventors have recognized that a problem to be solved includes providing a highly absorbent, disposable article, such as for use by incontinent individuals. The present inventors have recognized that the problem to be solved further includes providing a garment, such as a disposable brief or underpant that is lightweight compared to other highly absorbent articles of its class, is comfortable to wear for an extended duration, and is not bulky. In an example, the problem further includes providing an absorbent garment with a liquid acquisition speed that provides the wearer with a sense of dryness, particularly in or near insult areas. The problem further includes providing a highly absorbent, disposable article using readily available absorbent materials, such as wood pulp fluff (fluff) or super absorbent polymer (SAP) materials. The problem further includes selecting and arranging the absorbent materials to provide an article with improved liquid retention, for example, under load or when pressure is applied to a saturated or semi-saturated article.

In an example, a solution to these problems and others includes an absorbent article with three or more absorbent core structures. The three or more absorbent core structures can be at least partially overlapping in a stacked or layered configuration, such as in an expected insult zone of an absorbent article. The solution optionally includes a wearable absorbent garment with improved acquisition speed, reduced bulkiness, increased retention capacity, and improved perceived dryness, including over multiple insults.

In an example, the solution includes an absorbent article, such as a diaper, with a central region that includes the three overlapping core structures. A weight of the central region can comprise at least about 50%, 60%, or more of a total weight of the entire absorbent article. That is, most of the weight of the article, such as can be attributed to the absorbent material or materials comprising the core structures, can be positioned in the critical insult area.

This overview is intended to provide non-limiting examples of the present subject matter, and this overview is not intended to provide an exclusive or exhaustive explanation. The detailed description below is included to provide further information about the present disposable absorbent articles and related methods.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

Figure 1A:
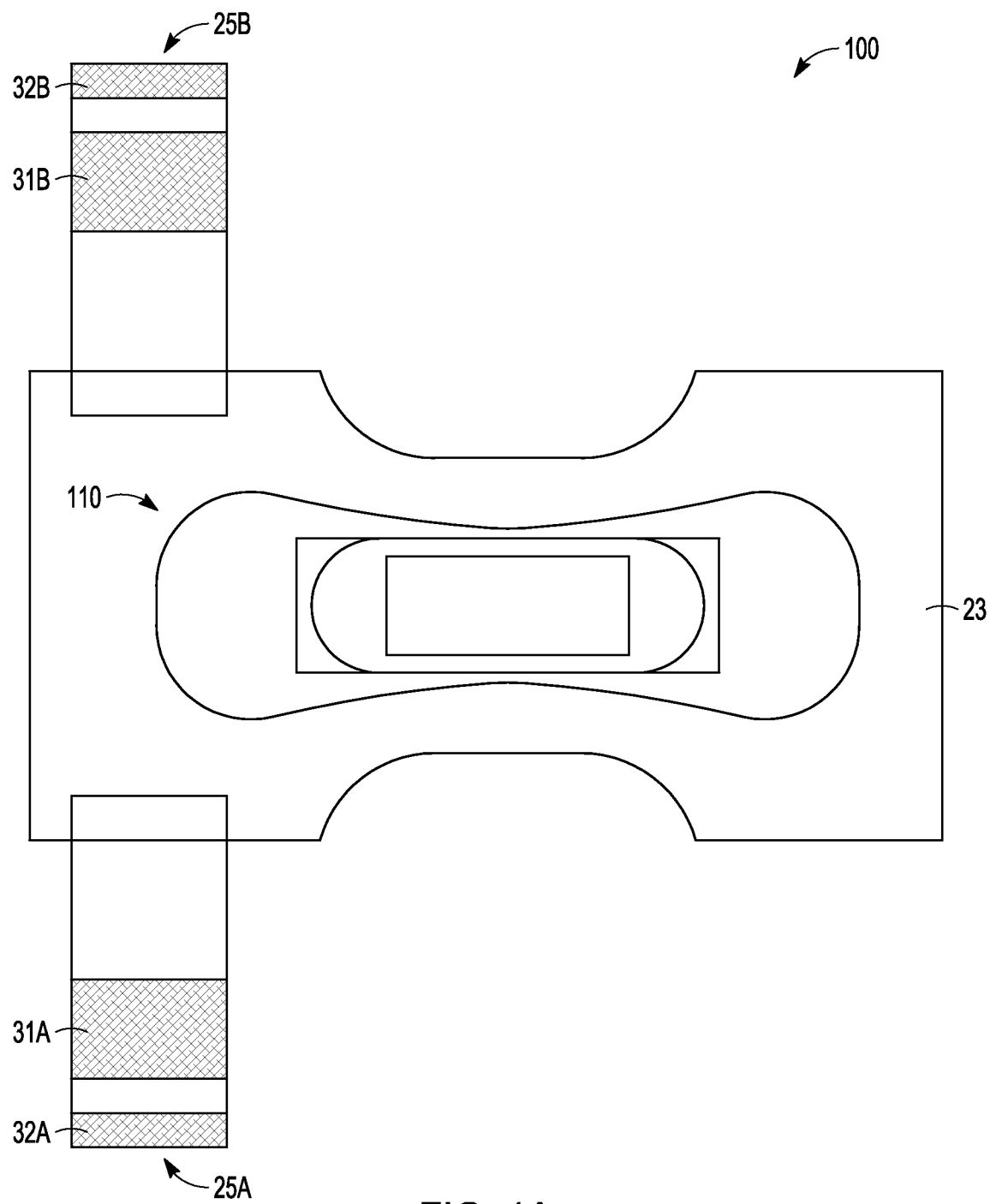
FIG. 1A illustrates generally a top plan view of an absorbent article having multiple core structures.

This detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. The present inventors also contemplate examples using any combination or permutation of the elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The present inventors have recognized that a problem to be solved includes providing a highly absorbent, disposable article, such as for use by incontinent individuals. The present inventors have recognized that the problem to be solved further includes providing a disposable garment that is relatively lightweight compared to other highly absorbent articles in a similar, high-absorbency class, is comfortable to wear for an extended duration, and is not bulky. Some classes related to such garments include overnight products, or high capacity products. The problem further includes providing an absorbent garment with an acquisition speed that provides the wearer with a sense of dryness, particularly in or near insult areas. The problem further includes providing a high absorbency disposable garment using readily available absorbent materials, such as wood pulp fluff (fluff) or super absorbent polymer (SAP) materials.

In an example, a solution to these problems includes an absorbent article with three or more absorbent core structures. Any two or more of the absorbent core structures can be at least partially overlapping in a stacked or layered configuration. Examples of an absorbent core assembly with multiple overlapping core structures are illustrated generally herein. The solution optionally includes a wearable absorbent garment with improved acquisition speed, reduced bulkiness, increased retention capacity, and improved dryness, including over multiple insults.

Although referred to herein as an "article", the high absorbency assembly with three or more absorbent core structures can take multiple different forms including, but not limited to: a wearable garment, such as a brief-style diaper; an article such as a pad that is wearable in combination with underwear or other garments; or a bed-pad type article that is configured to be placed beneath an individual, such as when the individual is seated or lying down.

In an example, an absorbent article with three or more absorbent core structures includes a non-woven top sheet, at least one acquisition distribution layer (ADL) configured to rapidly acquire and disperse liquid, an absorbent core assembly including a top absorbent core, a middle absorbent core, and a bottom absorbent core, a polymeric barrier film, and an outer non-woven bottom sheet. One or more of the absorbent core structures can include fluff, SAP, a combination of fluff and SAP, or some other absorbent material suitable for use in a disposable absorbent garment. In an example, one or more of the absorbent cores can be provided using a cut-and-placed airlaid material, or the one or more cores can be provided using respective discrete drum formers. In an example, different super absorbent polymers can be used in the respective different core structures, or different blends or ratios of multiple different super absorbent polymers can be used in the respective different core structures. Where multiple different types of polymers are used, the polymers can have different characteristics, such as different rates of absorption or rates of liquid acquisition, or different total absorbency under load (AUL) characteristics.

In some examples, a core structure can include multiple materials, such as SAP and fluff. The materials can be distributed substantially evenly or uniformly throughout the volume of the structure. That is, in an example that includes a core structure that includes both SAP and fluff, any given unit volume of the core structure can have substantially the same ratio of SAP to fluff. In other examples, a core structure can include multiple materials that are not distributed substantially evenly or uniformly throughout the volume of the structure. In these examples, at least one unit volume of the core structure can have a different ratio of constituent materials than at least one other unit volume of the same core structure.

In an example of a tri-core absorbent article, a relatively high concentration or volume of SAP can be provided at an insult zone. The insult zone includes a portion of an article where fluid is expected to be received when the article is worn or used. In an example, when the three discrete core structures are taken together and viewed as a core assembly, the concentration or density of SAP can be greater in the insult zone than the concentration or density of SAP in other areas that are peripheral to the insult zone, including in one or more other portions of a core assembly that do not include the insult zone. That is, an absorbent article can include a core assembly having an insult zone and a peripheral zone outside of the insult zone, and a SAP volume or concentration in the insult zone can be greater than a SAP volume or concentration in the peripheral zone. In an example, a greater volume or concentration of SAP at the insult zone can be provided by selecting for use in the core assembly one or more core structures that have different SAP volumes or concentrations. In an example, a greater volume or concentration of SAP at the insult zone can be provided by selecting for use at least one core structure having a different area than one or more of the other core structures in the assembly, and then overlaying the structures to provide a core assembly. Additionally or alternatively, a greater volume or concentration of SAP at the insult zone can be provided by selecting at least one core structure having a non-uniform SAP density, that is, a non-uniform distribution of SAP by volume over an area of the structure.

By concentrating the density of SAP in an insult zone of an absorbent article, several benefits can be realized. One benefit includes providing increased retention capacity because a greater portion of received fluid can be held by the SAP material than can otherwise be held by fluff or other materials, for example because fluff generally exhibits a lesser ability to retain fluids under load. Another benefit includes providing increased void volume, particularly in an insult zone. By providing increased void volume and increased retention capacity, a wearer can perceive the article as providing an improved sense of dryness, for example, when the article is used for an extended duration or when the article receives multiple insults.

Another benefit of concentrating SAP at an insult zone includes lowering a manufacturing cost of a high capacity absorbent article by removing all or a portion of the SAP from non-insult zone regions of the article. In an example of an article constructed according to the present disclosure, SAP is not distributed in high concentrations throughout all core structures. For example, SAP can be excluded from, or included in minimal volumes or concentrations in, absorbent structure areas that are less likely to receive fluid or are less likely to become saturated during normal use. For example, a middle core structure (see, e.g., FIG. 3) can have minimal or no SAP, such as in peripheral areas in front or back panels of a diaper. By minimizing or eliminating SAP from larger core structures, the per-unit cost of such structures is reduced. Any available SAP under a given budget can be applied in a relatively small, targeted insult zone, or in an area where fluid is expected to be received. By concentrating SAP in an insult zone, a high capacity article can be provided with improved retention and absorption/re-wet characteristics, such as shown herein in the test results illustrated in FIGS. 4-24.

In an example of a tri-core absorbent article, at least one of the core structures can include multiple materials that are not distributed substantially evenly or uniformly throughout the volume of the at least one core structure. For example, a core structure for use in a tri-core article can include SAP and fluff. The core structure can include a first unit volume having a first ratio of SAP to fluff (e.g., a first SAP volume or concentration, such as by weight or by volume), and the core structure can include a second unit volume having a second greater ratio of SAP to fluff (e.g., a second greater SAP density). In this example, the second unit volume having the second greater ratio of SAP to fluff can correspond to an expected insult zone when the article is worn. That is, when worn, the article includes a core assembly that provide a greater amount of SAP in an expected insult zone, and a lesser amount of SAP in areas outside of, adjacent to, or peripheral to the expected insult zone.

In an example of a tri-core absorbent article, two or more of the core structures can have different areas and/or different SAP volumes or concentrations. For example, a first article can include top and bottom core structures having substantially the same areas and SAP volumes or densities. The first article can include a middle core structure having a lesser area and, optionally, a different SAP volume or concentration than is provided in the top and bottom core structures. When assembled, the top, middle, and bottom core structures can be arranged to provide a core assembly with an SAP volume or concentration that is greater in an expected insult zone than in other, peripheral areas of the article when the article is worn. The bottom core structure can be registered to or aligned with the insult zone to improve fluid acquisition and retention characteristics, such as without increasing a total weight or cost of the article.

FIG. 1A illustrates generally an example of a top plan view of an absorbent article 100 having a tri-core assembly 110 with three substantially distinct core structures. The article 100 is a diaper with left and right side panel assemblies 25A and 25B that extend from opposite sides of a back panel of a nonwoven backsheet 23. In an example, the left and right side panel assemblies 25A and 25B include respective extensible and retractable portions 31A and 31B and fasteners 32A and 32B for providing a secure and comfortable fit for a wearer. In other examples, an article with the tri-core assembly 110 can be prefastened, or can have a continuous waistband to provide an underwear-like product. In other examples, an article with the tri-core assembly 110 includes a bed pad, such as a substantially flat structure without a fastener or closure element, but optionally including means to maintain the structure in a placed configuration, such as adhesive or rubberized portions.

Figure 1B:
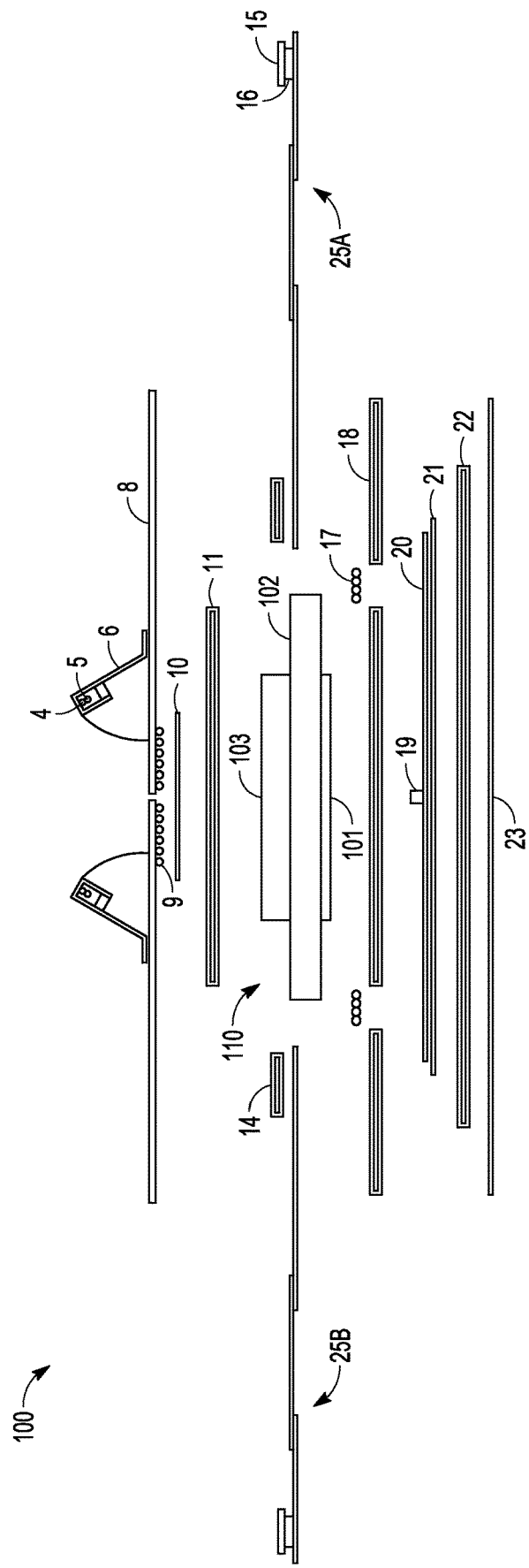
FIG. 1B illustrates generally an example of an exploded cross-section view of an absorbent article having multiple core structures.

FIG. 1B illustrates generally an example of an exploded cross-section view of the absorbent article 100 of FIG. 1A, including the tri-core assembly 110. In an example, the nonwoven backsheet 23 extends over all or at least a portion of the article, and the nonwoven backsheet 23 provides a garment-facing surface of the article 100 when the article is worn under clothing. The article 100 includes a liquid-impermeable polymeric barrier layer 21, and an adhesive layer 22 that is used to secure the polymeric barrier layer 21 to the nonwoven backsheet 23. Optionally, the article includes printing 20 over all or a portion of the surface of one or both of the nonwoven backsheet 23 or the polymeric barrier layer 21. The printing can include graphic designs, size indicia, or other markings for aesthetic or functional purposes.

The article optionally includes a wetness indicator 19, such as can be positioned substantially centrally along a portion of a length of the article. Leg elastics 17 and leg elastic adhesives 18 are layered between any two or more of the nonwoven backsheet 23, the polymeric barrier layer 21, and respective left and right side panel assemblies 25A and 25B. The leg elastics 17 extend substantially parallel to a longitudinal axis of the article 100 at or near leg cutouts.

The article 100 includes a tri-core assembly 110 that includes three absorbent core structures. Optionally, more than three core structures can be used. Optionally, one or more core structures can be used, and the one or more core structures can have a variable thickness, or can have non-homogeneously-distributed constituent parts. For example, a unitary but non-homogenous core structure can have a portion that comprises fluff without SAP and another portion that comprises fluff with SAP, and optionally another portion that comprises fluff with a different proportion of SAP relative to fluff.

The tri-core assembly 110 in the example of FIG. 1B includes a bottom core 101, a middle core 102, and a top core 103. One or more layers can optionally be interposed between the different core structures comprising the tri-core assembly 110, however, the example of FIG. 1B illustrates the core structures as being stacked directly on top of one another. For example, an acquisition/distribution layer can optionally be interposed between any two of the core structure layers.

The article 100 further includes side panel attachment means 14, a side panel fastener 15, and side panel fastener adhesive 16. The attachment means 14 can include an adhesive, an ultrasonic bond, a breakable fastener, or other means of securely attaching non-woven, laminate, polymeric, or other materials. The article 100 includes a top sheet 8, such as can be a non-woven cloth. A core adhesive 11 and an acquisition/distribution layer 10 (ADL), such as with a corresponding ADL adhesive 9, can be positioned between the top sheet 8 and the tri-core assembly 110. Optionally, the article 100 includes a stand-up leg elastic assembly 6, including a nonwoven material, one or more elastic components 5, and an adhesive 4.

Figure 2A:
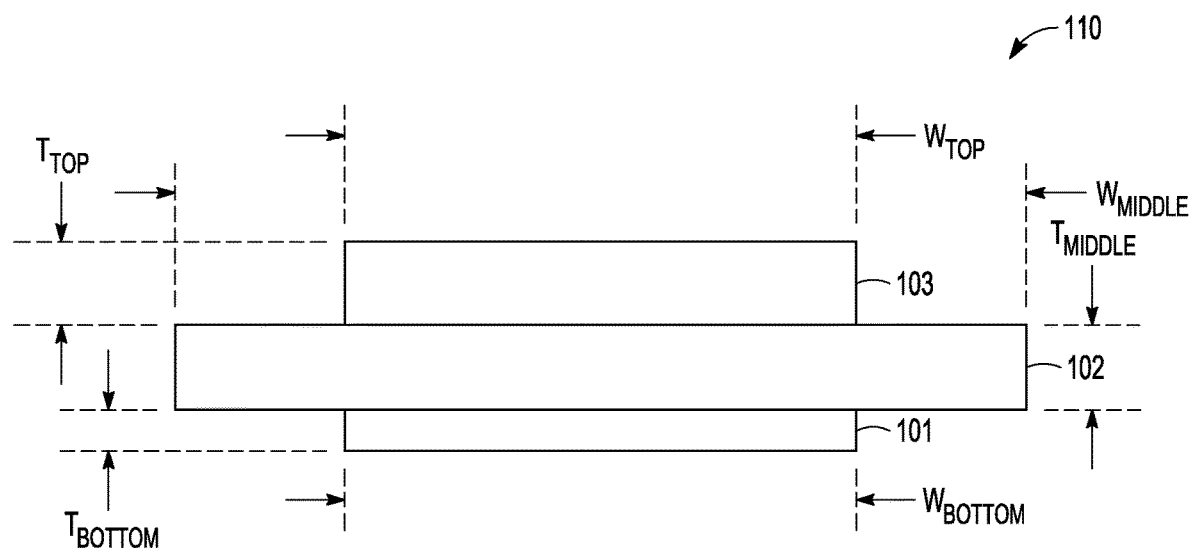
FIGS. 2A and 2B illustrate generally examples of detail cross-section views of multiple core absorbent assemblies.

FIG. 2A illustrates generally a first example of a detail cross-section view of the tri-core assembly 110 including the bottom core 101, middle core 102, and top core 103 structures from the example article 100 of FIGS. 1A and 1B. The relative thicknesses and widths of the discrete bottom, middle, and top core structures can be adjusted to influence various characteristics of the article. For example, a rate of liquid acquisition, an overall article weight, thickness or size, or an article liquid retention capacity, can be determined in part by selecting different thicknesses or widths for the different core structures.

In the example of FIG. 2A, each of the bottom core 101, middle core 102, and top core 103 structures is a unitary element. That is, each core structure is formed separately and then assembled with the other core structures to provide the tri-core assembly 110. Optionally, the tri-core assembly 110 is formed in-line by layering one core structure on another, such as with or without another interposing layer, adhesive, or substrate.

In the example of FIG. 2A, a thickness of the top core 103 $T_{TOP}$ is substantially the same as a thickness of the middle core 102 $T_{MIDDLE}$, that is, $T_{TOP} \approx T_{MIDDLE}$. The bottom core 101 has a lesser thickness $T_{BOTTOM}$ than either of the top and middle cores 103 and 102. In the example of FIG. 2A, a width of the top core $W_{TOP}$ is substantially the same as a width of the bottom core 101 $W_{BOTTOM}$, that is, $W_{TOP} \approx W_{BOTTOM}$. The middle core 102 has a width $W_{MIDDLE}$ that is greater than the widths of the top and bottom cores 103 and 101. In an example, the bottom core 101 includes a greater concentration or density of SAP per unit volume of the bottom core 101 than a SAP density in one or both of the middle and top cores 102 and 103.

Figure 2B:
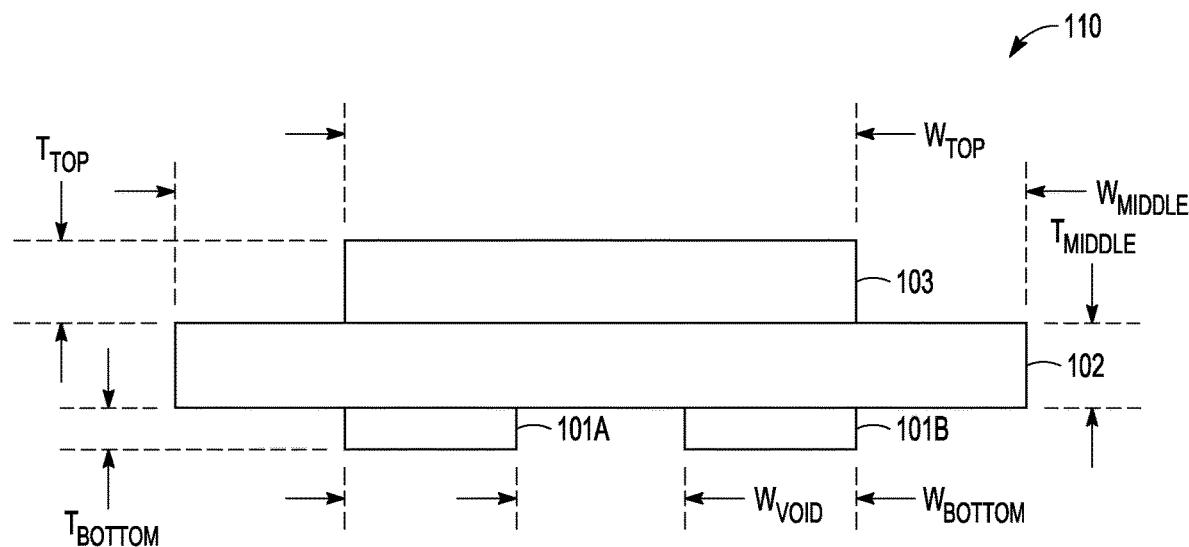

FIG. 2B illustrates generally a second example of a detail cross-section view of a core assembly 112, such as can optionally be used with the article 100 instead of the tri-core assembly 110. In the example of FIG. 2B, at least one of the discrete absorbent core structures from the example of FIG. 2A can be replaced with two or more discrete structures. For example, in FIG. 2B, the core assembly 112 includes the middle core 102 and top core 103, as in FIG. 2A, and further includes first and second bottom core structures 101A and 101B. The first and second bottom core structures 101A and 101B are separated from each other by a void width $W_{VOID}$, such as along a longitudinal centerline of the absorbent article. With respect to the example of FIG. 2A, a portion of the bottom core 101 can be considered to have been "removed" in the example of FIG. 2B, to thereby provide the first and second bottom core structures 101A and 101B. By removing a portion of an absorbent core as shown in FIG. 2B, a per-unit cost can be reduced, such as because an amount of SAP or other absorbent material can be reduced, while at least some of the functional benefit of having multiple core structures is preserved. In an example, the middle core 102 includes a fluff core that distributes liquid across its width and into the first and second bottom core structures 101A and 101B, such as when an insult is received at or near the longitudinal centerline of the article, corresponding to the void width between the first and second bottom core structures 101A and 101B.

One or more of the other core structures can optionally be formed from multiple discrete core structures. The structures can be separated along the longitudinal centerline, as in the example of FIG. 2B, or can be separated along other paths. For example, two or more sections of a core can be positioned along the longitudinal centerline but separated by a specified distance. In some examples, at least one of the cores can be perforated, such as to increase liquid throughput to an adjacent core structure, or to reduce a mass of the structure. Generally, unitary or other core structures are positioned such that they are mostly or entirely in an overlapping fashion at or near an expected insult zone of an absorbent article.

Figure 3:
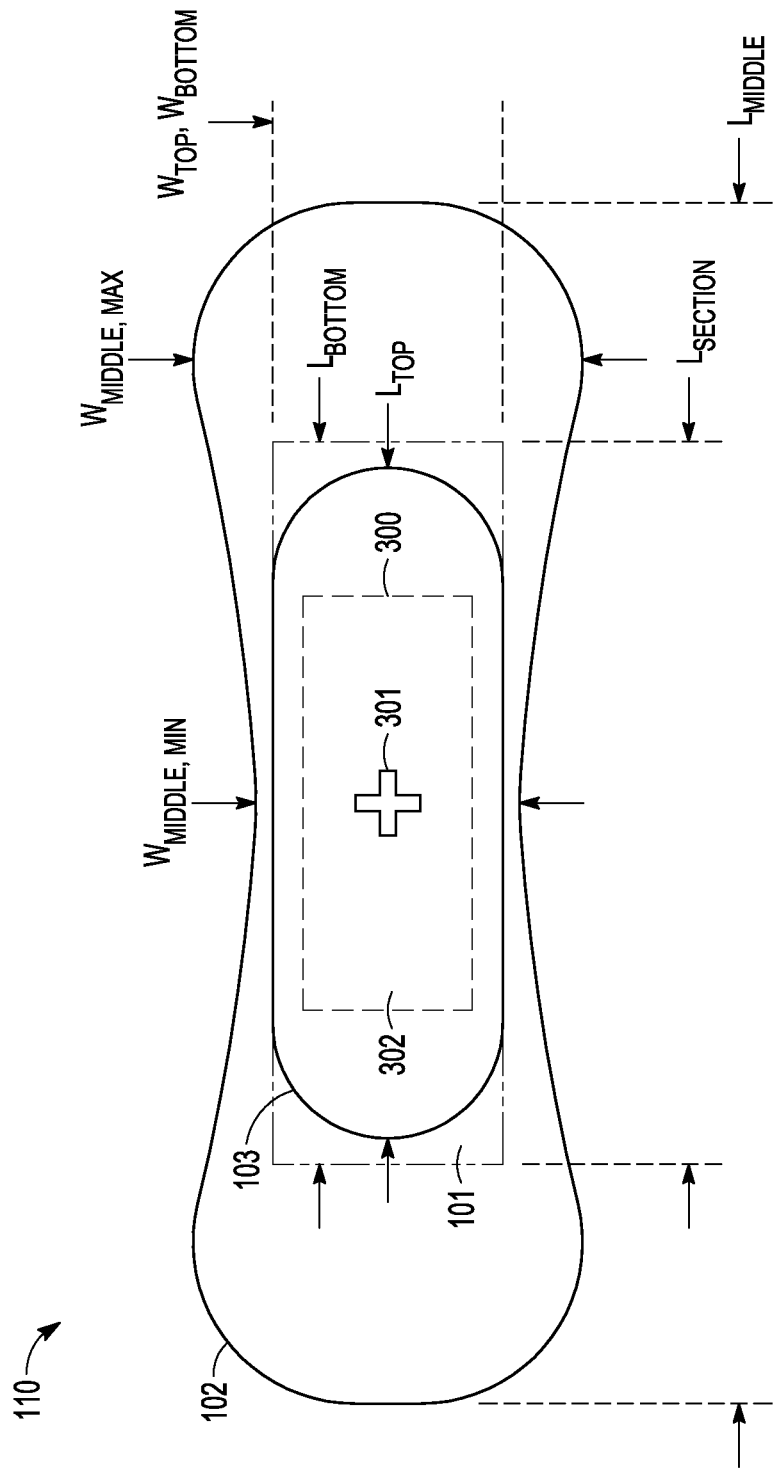
FIG. 3 illustrates generally an example of a top view of a multiple core absorbent assembly

FIG. 3 illustrates generally an example of a top view of the tri-core assembly 110. FIG. 3 further illustrates an expected insult zone 300, including an insult target 301 (indicated by the "+") and a peripheral insult area 302 (indicated by the dashed-line rectangle). In this example, the bottom core 101 and the top core 103 overlap in a region that corresponds to the insult zone 300. In this example, the insult zone 300 has a body-side surface area that is less than a body-side surface area of any of the top, middle, and bottom core structures. In other examples, the insult zone can be extended to include an area with a body-side surface area that is approximately the same as one or more of the core structures in the tri-core assembly 110.

In the example of FIG. 3, the top, middle, and bottom core structures have different dimensions and different shapes. The top core 103 has an oval-shaped structure having a width $W_{TOP}$ and a length $L_{TOP}$. The middle core 102 has a substantially hourglass-shaped structure having a maximum width $W_{MIDDLE,MAX}$, a minimum width $W_{MIDDLE,MIN}$, and a length $L_{MIDDLE}$. The bottom core 101 (illustrated in FIG. 3 with broken lines) has a rectangular shape having a width $W_{BOTTOM}$ and a length $L_{BOTTOM}$. As shown, the top core 103 and bottom core 101 have substantially the same width. The top core 103 and bottom core 101 have approximately the same length, with the top core length $L_{TOP}$ being slightly less than the bottom core length $L_{BOTTOM}$.

Although the top, middle, and bottom cores 103, 102, and 101 are shown in FIG. 3 as having different shapes, in other examples, two or more of the core structures can have substantially similar or identical shapes. For example, the top and bottom core structures can optionally both be rectangular, or can optionally both be substantially oval-shaped. Other shapes can be selected based on desired absorption characteristics, insult zone surface area, or target fit. As described above and illustrated in FIG. 3, the three core structures can each be a unitary core structure that is layered in an overlapping manner at the insult zone 300 to provide the tri-core assembly 110. In other examples, one or more of the core structures can include segments or portions that are discontinuous, such as to conserve material and reduce cost.

In the example of FIG. 3, the bottom core 101 has an outer periphery that falls substantially within the contours of the middle core 102. That is, a top surface area of the bottom core 101 is substantially covered by the adjacent, middle core 102. In an example, the width of the bottom core 101, $W_{BOTTOM}$, is less than or equal to the width of the middle core 102, $W_{MIDDLE,MIN}$. Additionally, the length of the bottom core 101, $L_{BOTTOM}$, can be less than or equal to the length of the middle core 102, $L_{MIDDLE}$.

In an example, the top core 103 has an outer periphery that falls substantially within the contours of the middle core 102. That is, a bottom surface area of the top core 103 is substantially covered by the adjacent, middle core 102. In an example, the width of the top core 103, $W_{TOP}$, is less than or equal to the minimum width of the middle core 102, $W_{MIDDLE,MIN}$. Additionally, the length of the top core 103, $L_{TOP}$, can be less than or equal to the length of the middle core 102, $L_{MIDDLE}$.

The top, middle, and bottom core structures can have different compositions. As used herein, the term "composition" refers to a combination of different parts, materials, or elements that make up a structure. In some examples, a core can have a composition that includes one material, such as a wood pulp fluff material, and in other examples, a core can have a composition that includes multiple materials, such as a mixture of fluff, SAP, or other absorbent materials. In an example that includes the tri-core assembly 110, any one or more of its core structures can have a different absorbency under load (AUL) characteristic. For example, the bottom core 101 can have a higher AUL characteristic than one or both of the top and middle cores 103 and 102. In an example, any one or more of the top, middle, and bottom cores 103, 102, and 101, can be substantially or entirely polymer-based (i.e., substantially or entirely free of fluff pulp).

In an example, the top core 103 includes a mixture of about two parts fluff to one part of SAP. The middle core 102 can include a mixture of about forty parts fluff to one part of SAP. The bottom core 101 can include an airlaid material, such as including one or more of fluff and SAP. In an example, the bottom core 101 includes an airlaid mixture of fluff and SAP contained between top and bottom tissue (e.g., non-woven) layers.

In an example, one or more interposing layers can be positioned between any of the top, middle, and bottom cores 103, 102, and 101. For example, a first acquisition/distribution layer can be positioned between the top core 103 and the middle core 102, and a second acquisition/distribution layer can be positioned between the middle core 102 and the bottom core 101. The one or more interposing layers can be selected to optimize liquid distribution, dispersion, or exchange between and among the various core structures. In the example of FIG. 1, the article includes a single acquisition/distribution layer 10 positioned on a body-side of the top core 103, such as adjacent to the top sheet 8.

The three cores of the tri-core assembly 110 overlap in the insult zone 300 as described above. Two or more of the three cores overlap in areas outside of the insult zone 300 but inside of a central section of an absorbent article that includes the tri-core assembly 110. In the example of FIG. 3, the central section corresponds to a length, $L_{SECTION}$, of the tri-core assembly 110 that extends to opposite ends of the bottom core 101. That is, $L_{SECTION}$ is coterminous with $L_{BOTTOM}$. Optionally, $L_{SECTION}$ can be coterminous with the insult zone 300, with the top core 103, or with the middle core 102. In an example, a cross-section corresponding to $L_{SECTION}$ of an absorbent article can have about 60% of the weight of the total absorbent article. That is, the central section of the tri-core assembly 110 of an absorbent article can be characterized in that its corresponding cross-section of the absorbent article has a mass characteristic that is at least about 60% of a total mass characteristic of the absorbent article. In an example, the central section of the tri-core assembly 110 has a mass characteristic that is at least about 70% of a total mass characteristic of the tri-core assembly 110. In an example, $L_{SECTION}$ corresponds to about 55% of the total maximum length of the core assembly, $L_{MIDDLE}$.

Generally, when absorbent material is added to a core structure, overall absorbent capacity can be increased. However, the increase in capacity can come at the expense of, e.g., reduced acquisition speed or lesser retention capability. FIGS. 4-15 illustrate generally results of a series of experiments conducted using tri-core and traditional absorbent products. As shown, articles prepared with a tri-core absorbent assembly, such as according to the systems and methods described herein, outperform high capacity articles that are constructed in other ways.

The experimental results were obtained by performing a series of tests for various groups of absorbent articles of corresponding sizes (generally designated "Large"). For each test, several groups including ten articles each were tested, and the average results for each group of articles are tabulated. The articles under test are labeled Article L-1, L-2, and so on, through L-11. For brevity, the labels "Article L-χ" refer to respective mean characteristics of multiple, similarly-constructed articles of the same type (i.e., articles of the same size and of the same group, brand, or model). In the examples of FIGS. 5-15, Articles L-2 were each prepared with a tri-core assembly, such as including the top, middle, and bottom cores 103, 102, and 101, as described herein at least at FIGS. 2A and 3. The other articles under test have single or dual-core construction, as detailed in Table 1.

TABLE 1

Table of Articles tested; see FIGS. 4-15.

| Article | Characteristic |
|---|---|
| Article L-1 | Dual-core construction |
| Article L-2 | Tri-core construction |
| Article L-3 | Single-core construction |
| Article L-4 | Dual-core construction |
| Article L-5 | Dual-core construction |
| Article L-6 | Single-core construction |
| Article L-7 | Single-core construction |
| Article L-8 | Dual-core construction |
| Article L-9 | Dual-core construction |
| Article L-10 | Dual-core construction |
| Article L-11 | Single-core construction |

Figure 4:
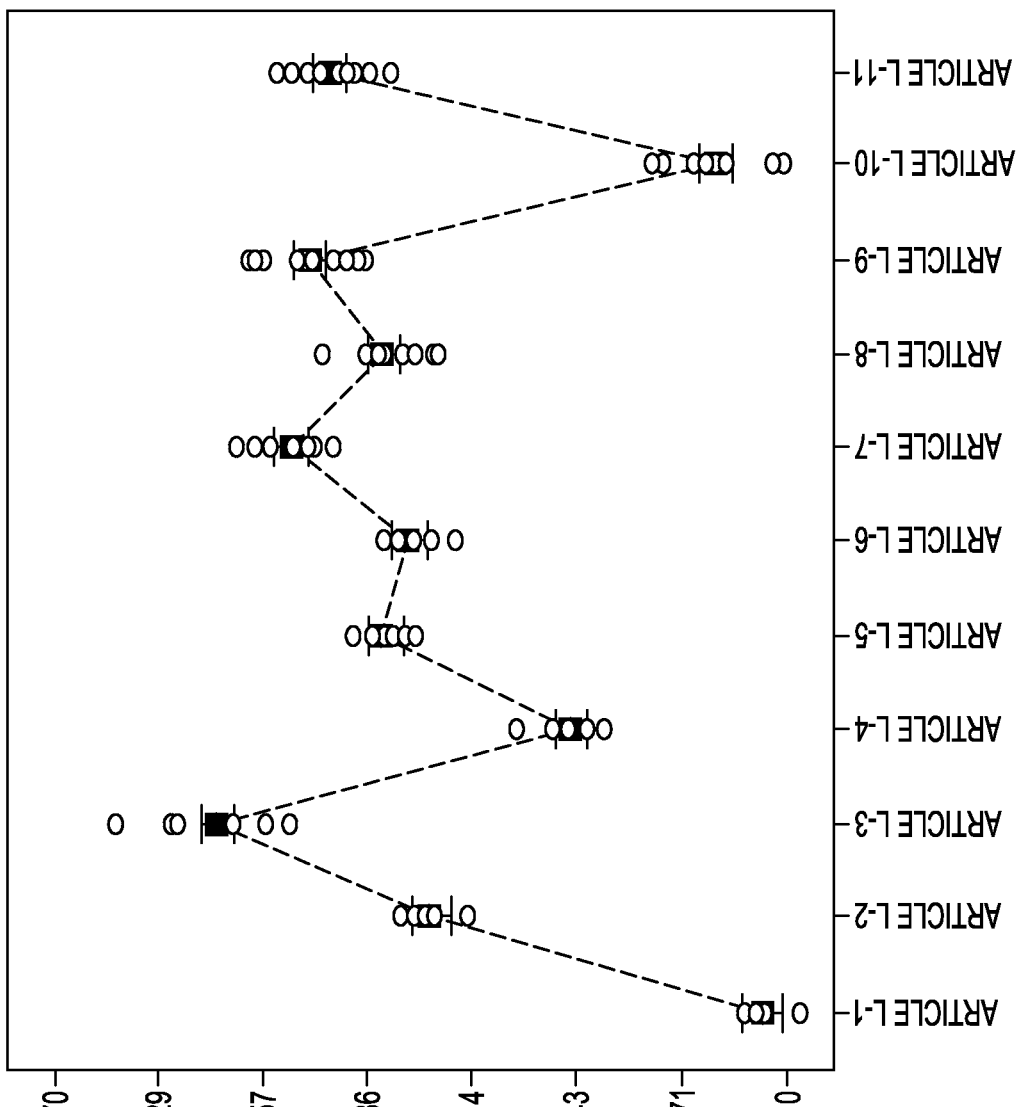
FIG. 4 illustrates generally measured dry weight characteristics for multiple absorbent articles.

First, a dry weight of each article was measured before any liquid was introduced (see FIG. 4). FIG. 4 shows that the dry weight of Article L-2, prepared with a tri-core absorbent assembly according to the present disclosure, is less than the other articles under test.

FIGS. 5-10 illustrate generally results from a series of liquid insult test. A series of three 200 ml liquid saline insults were provided in substantially corresponding locations for each article under test. In the examples of Article L-2 including a tri-core assembly, such as corresponding to the example of FIG. 3, the insults were provided substantially at or near the insult target 301. The multiple 200 ml liquid saline insults were administered at 10 minute intervals. The rate of acquisition for each 200 ml insult was measured.

Figure 5:
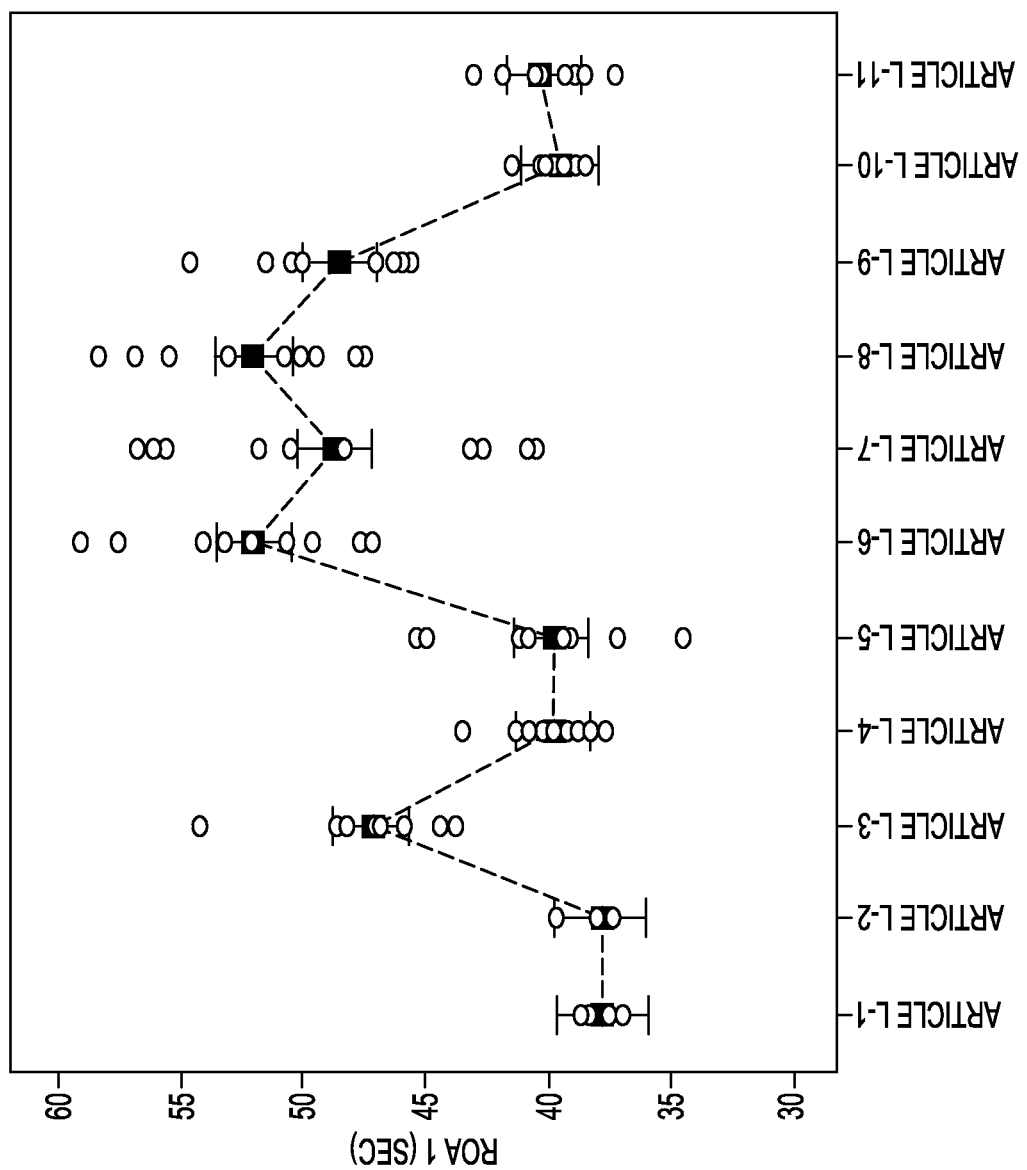
FIG. 5 illustrates generally experimental results showing rates of liquid acquisition following a first simulated insult for multiple absorbent articles.

FIG. 5 illustrates generally mean rates of acquisition for a first 200 ml insult for the Large articles. FIG. 5, for example, illustrates generally a first mean rate of acquisition for 200 ml of liquid saline for the multiple articles under test. The rate of acquisition indicates generally how quickly the insult was absorbed by each article. A lesser rate indicates that the sample insult was absorbed more quickly. The mean rate of acquisition for Article L-2, corresponding to a tri-core absorbent assembly of the present disclosure, was 37.87 seconds, which is among the least of the various different articles under test.

Figure 6:
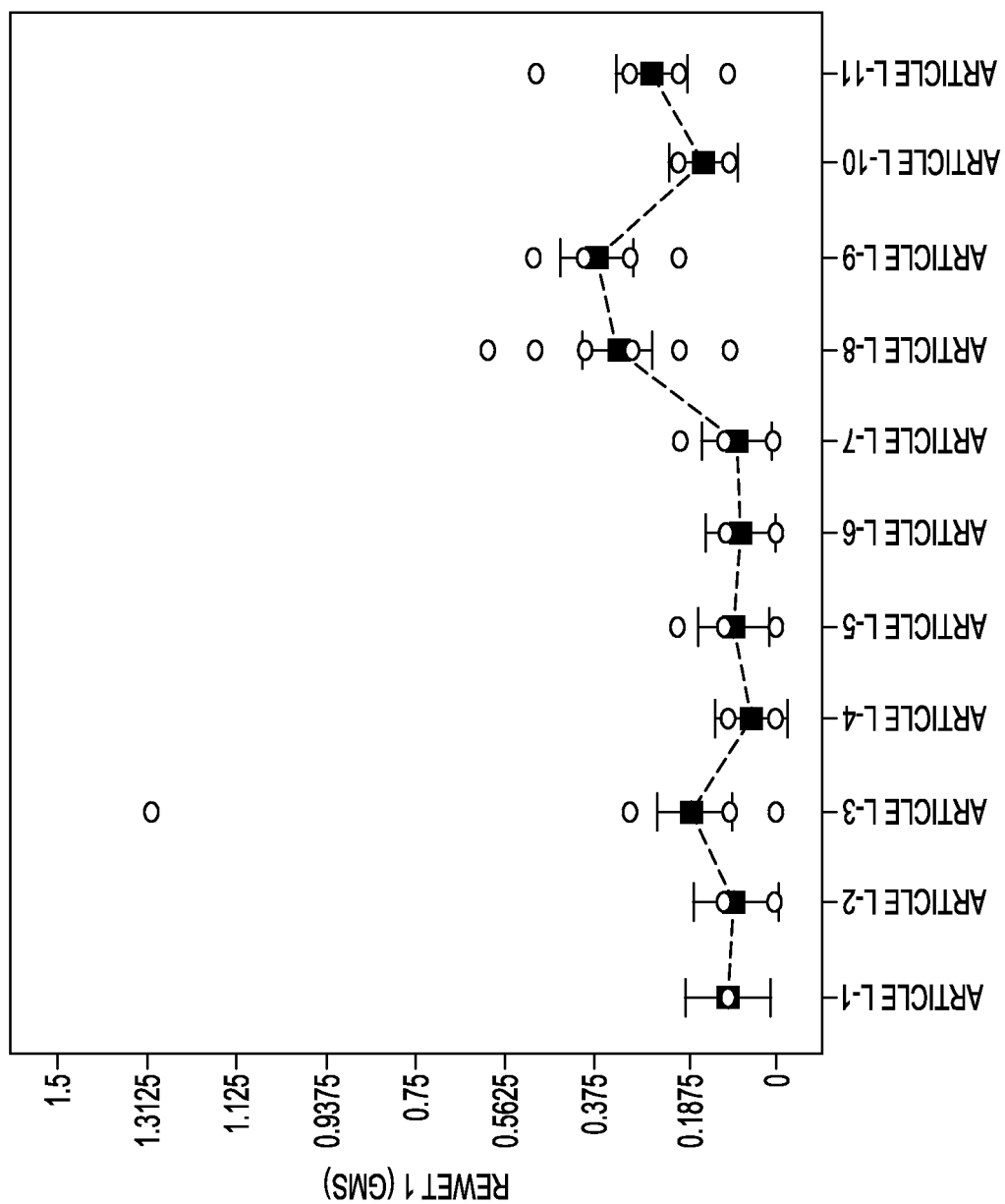
FIG. 6 illustrates generally experimental results showing rewet characteristics for multiple absorbent articles following a first simulated insult.

FIG. 6 illustrates generally rewet characteristics for the Large articles after the first 200 ml insult. To measure a rewet characteristic, an absorbent filter paper is placed on the top of each tested article, under 10 pounds of pressure, for 1 minute. The filter paper is then removed, weighed, and the rewet characteristic, or strikeback wetness, is determined based on the weight of the wetted filter paper. Generally, a saturated fluff-based absorbent core will release more of its liquid than a similarly-saturated SAP-based absorbent core. A lesser weight indicates that the article under test retained more of the liquid from the insult. A greater weight indicates that the article under test released or gave up a relatively greater amount of the insult liquid.

Figure 7:
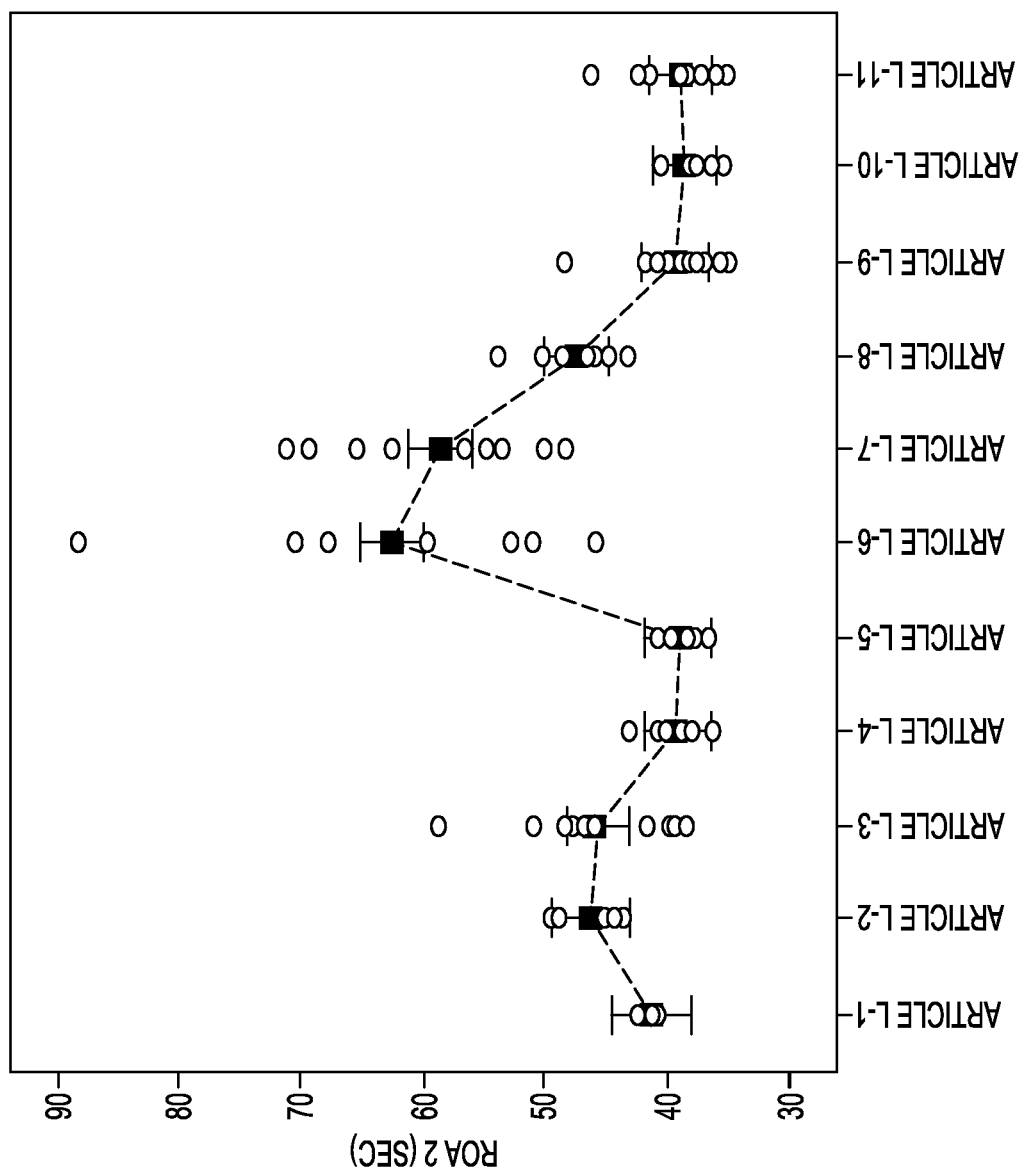
FIG. 7 illustrates generally experimental results showing rates of liquid acquisition following a second simulated insult for multiple absorbent articles.
Figure 8:
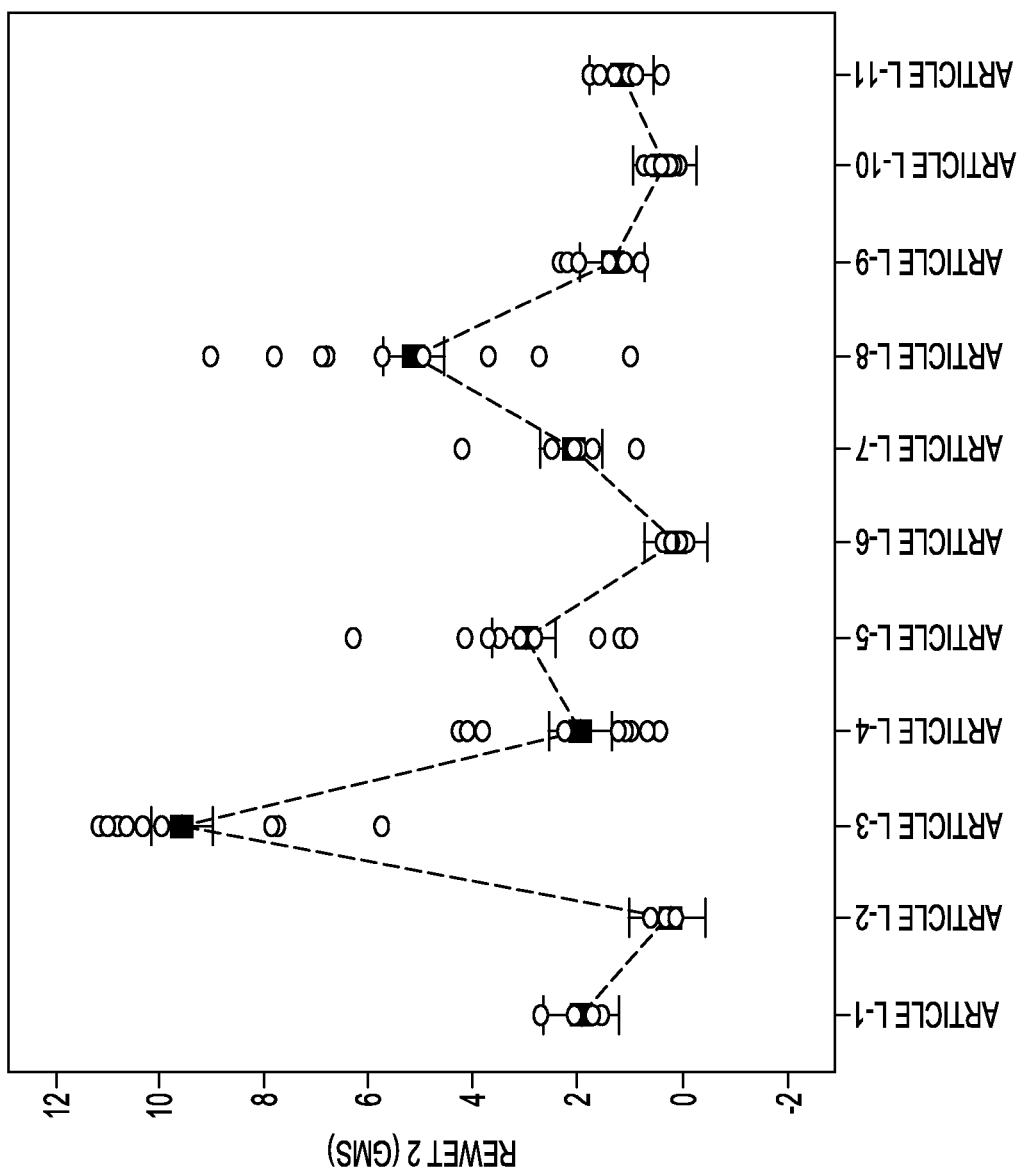
FIG. 8 illustrates generally experimental results showing rewet characteristics for multiple absorbent articles following a second simulated insult.
Figure 9:
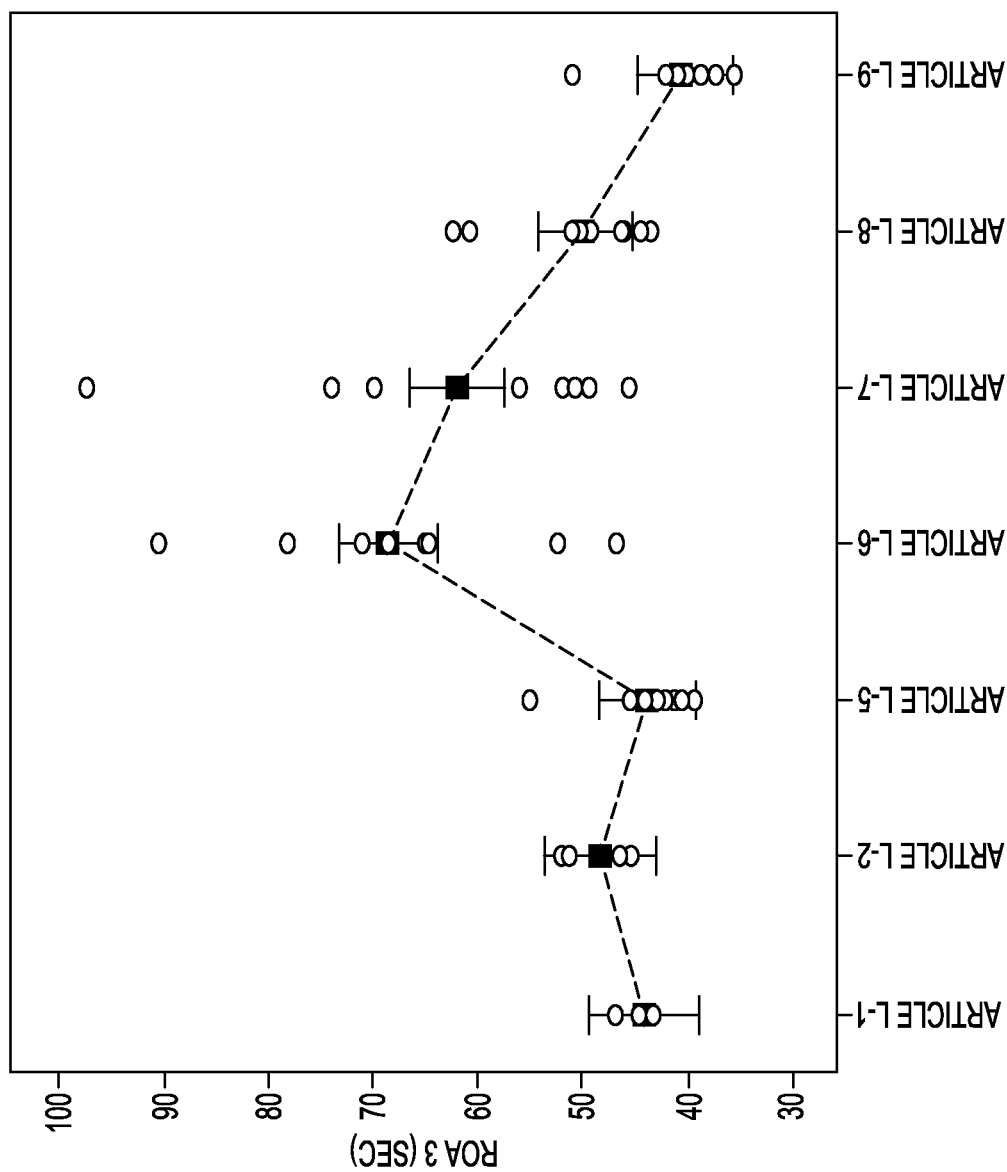
FIG. 9 illustrates generally experimental results showing rates of liquid acquisition following a third simulated insult for multiple absorbent articles.
Figure 10:
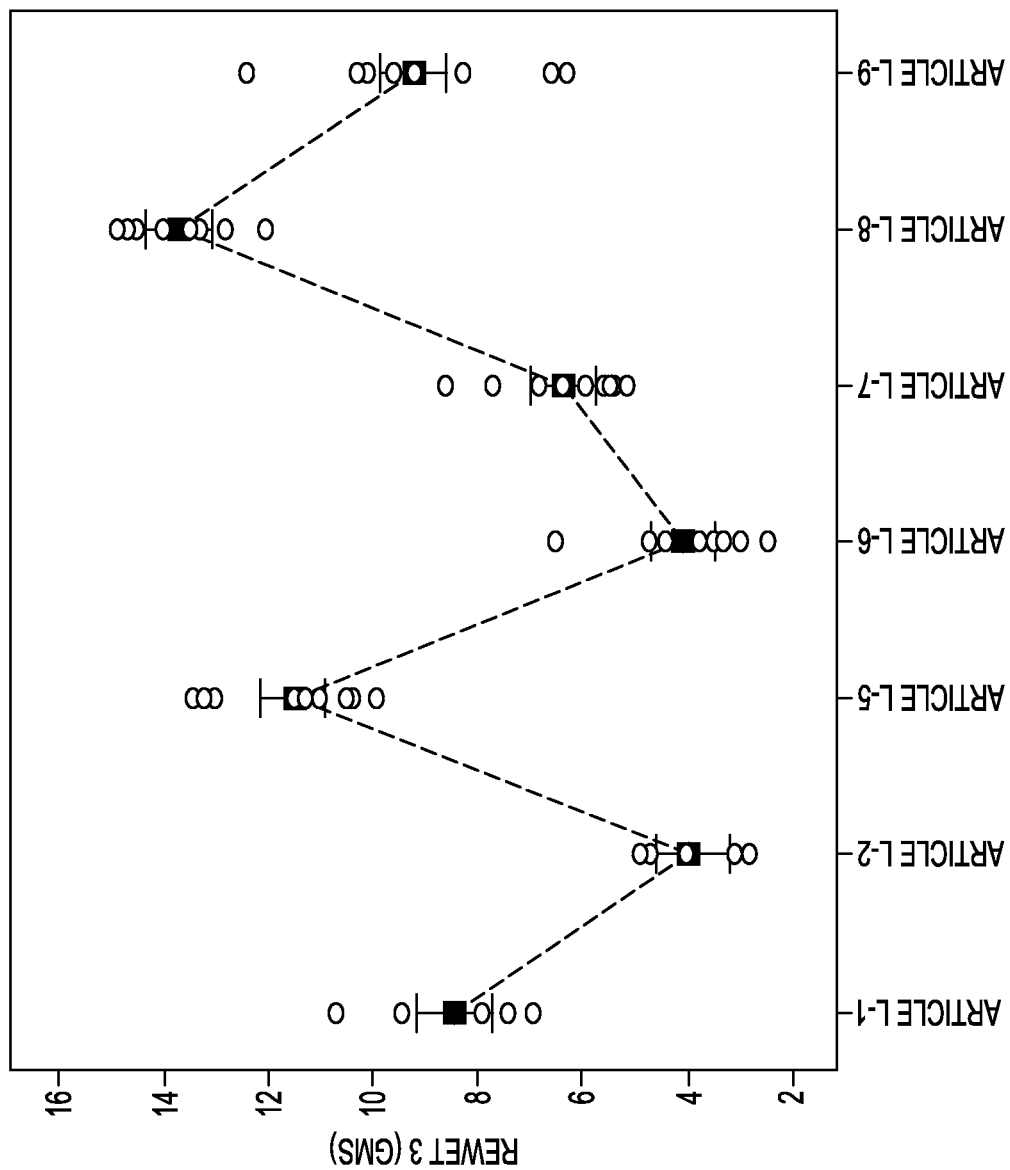
FIG. 10 illustrates generally experimental results showing rewet characteristics for multiple absorbent articles following a third simulated insult.

FIG. 7 illustrates generally mean rates of acquisition for a second 200 ml insult for the Large articles. FIG. 8 illustrates generally rewet characteristics for the Large articles following the second 200 ml insult. FIG. 9 illustrates generally mean rates of acquisition for a third 200 ml insult for the Large articles, and FIG. 10 illustrates generally rewet characteristics for the Large articles following the third 200 ml insult. After the third insult, Article L-2 showed the least rewet on average among the sample set of articles.

Figure 11:
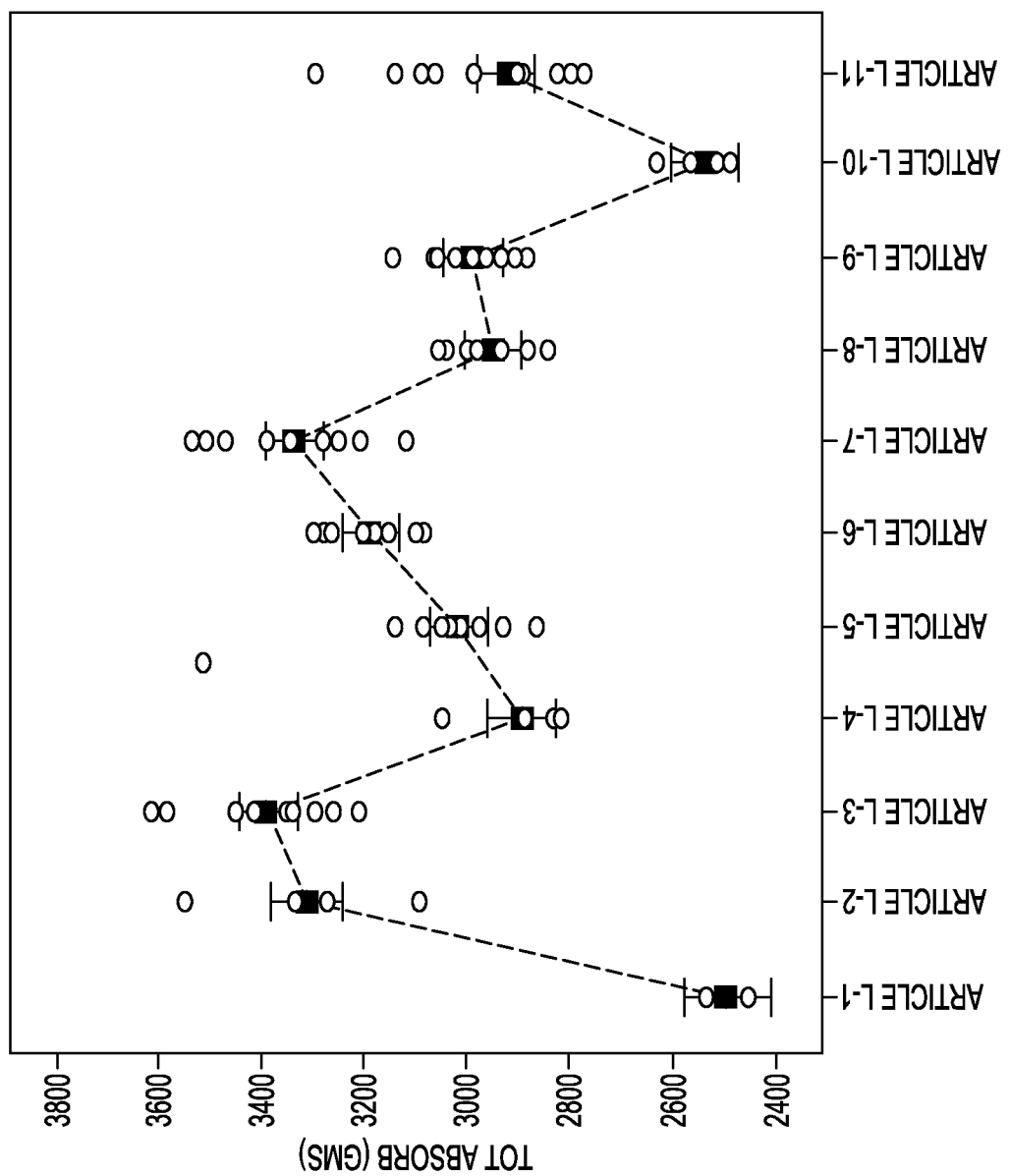
FIG. 11 illustrates generally experimental results showing total absorbency characteristics for multiple absorbent articles.
Figure 12:
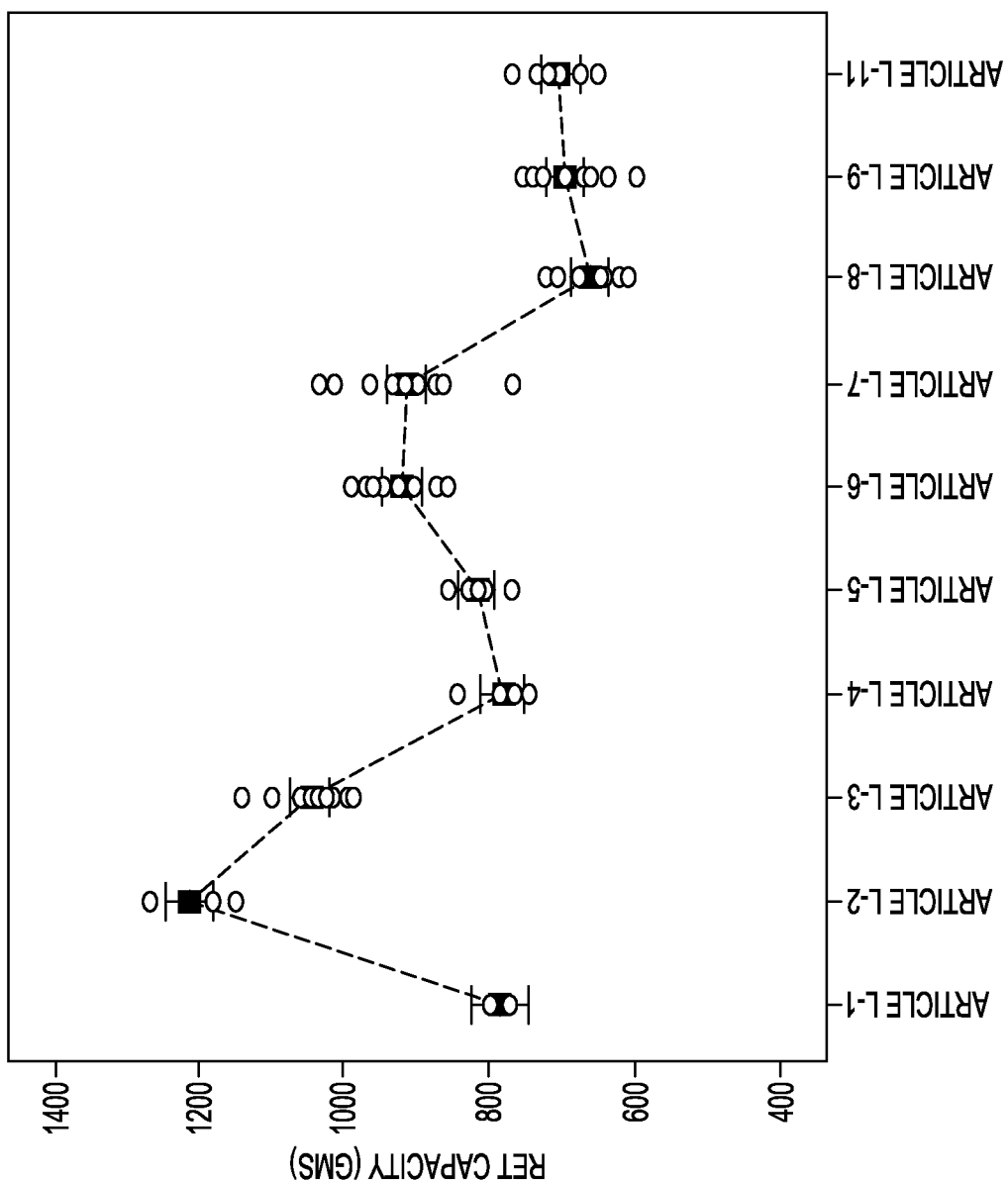
FIG. 12 illustrates generally experimental results showing liquid retention characteristics for multiple absorbent articles.

FIG. 11 illustrates generally total absorbency characteristics for the tested articles, and FIG. 12 illustrates generally retention capacity characteristics for the articles under test. Total absorbency is measured by submerging an entire sample article in a saline solution until the sample is saturated. The saturated sample article is then weighed. Under this test, a total capacity of a sample is measured without load pressure. Retention capacity is measured by applying a load or weight to a saturated sample article for a given sample period, draining away any liquid that is discharged, and then weighing the sample. In an example, a retention capacity test can provide an indication of how an article performs in-situ. For example, results of a retention test can be used to indicate how well a saturated or partially-saturated article will perform when a patient wearing the article sits or lies down. Generally, fluff is sponge-like and exhibits relatively little retention capacity under load, whereas SAP can have a retention capacity of, for example, 20 to 60 grams of liquid retained per gram of SAP material under load.

FIG. 11 illustrates generally a mean total absorbency for each of the Large articles L-1 through L-11, and FIG. 12 illustrates generally a mean retention capacity for each of the Large articles L-1 through L-11. As shown, Article L-2, including the tri-core absorbent assembly according to the present disclosure, performs on average about the same as articles L-3 and L-7 for total absorbency. Under load, Article L-2 outperforms most of the articles by about 30% or more, and Article L-2 outperforms article L-3 by about 168 grams on average.

Figure 13:
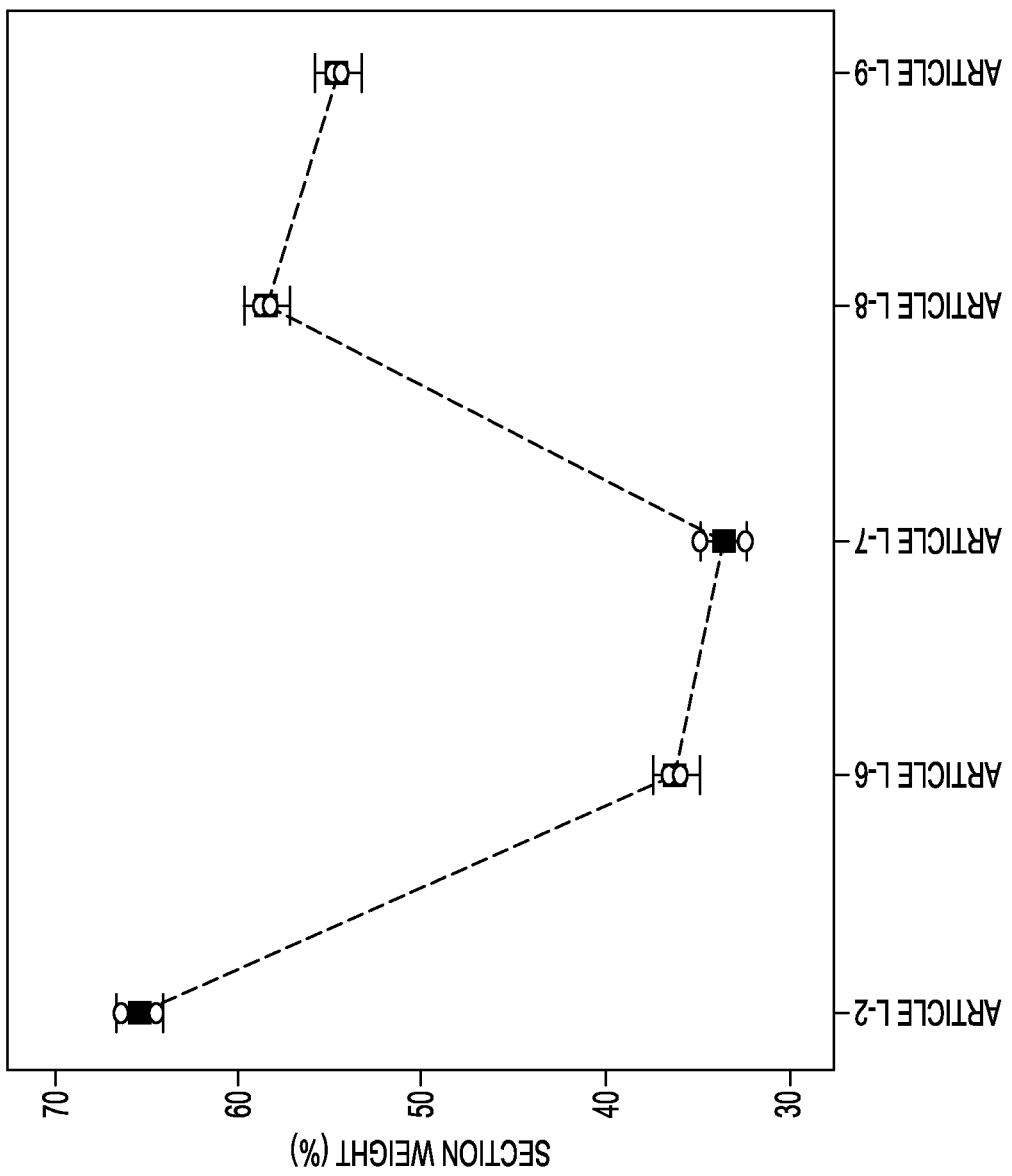
FIG. 13 illustrates generally measured dry weight characteristics for central cross-section regions from multiple absorbent articles.
Figure 14:
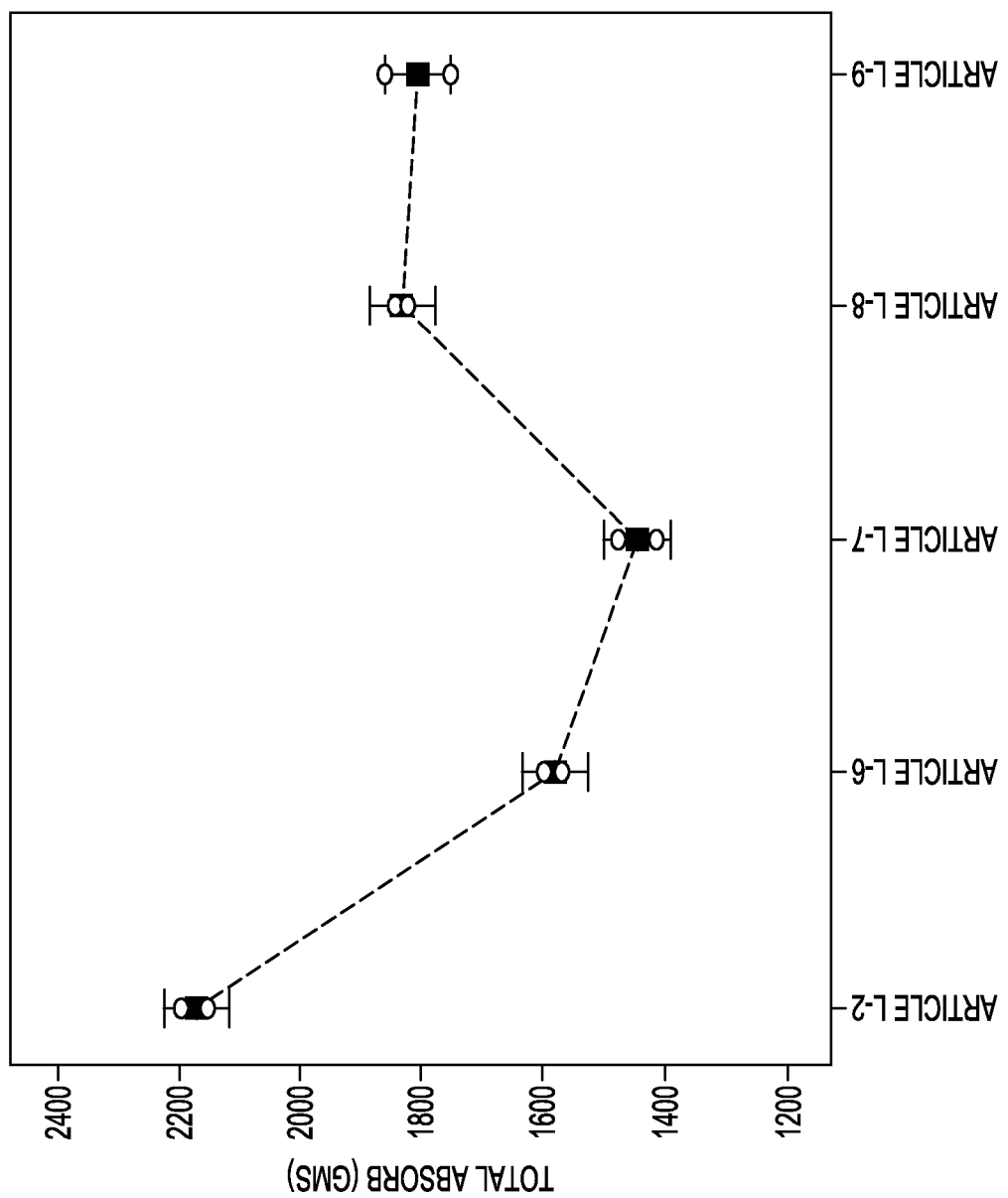
FIG. 14 illustrates generally experimental results showing total absorbency characteristics for central cross-section regions from multiple absorbent articles.
Figure 15:
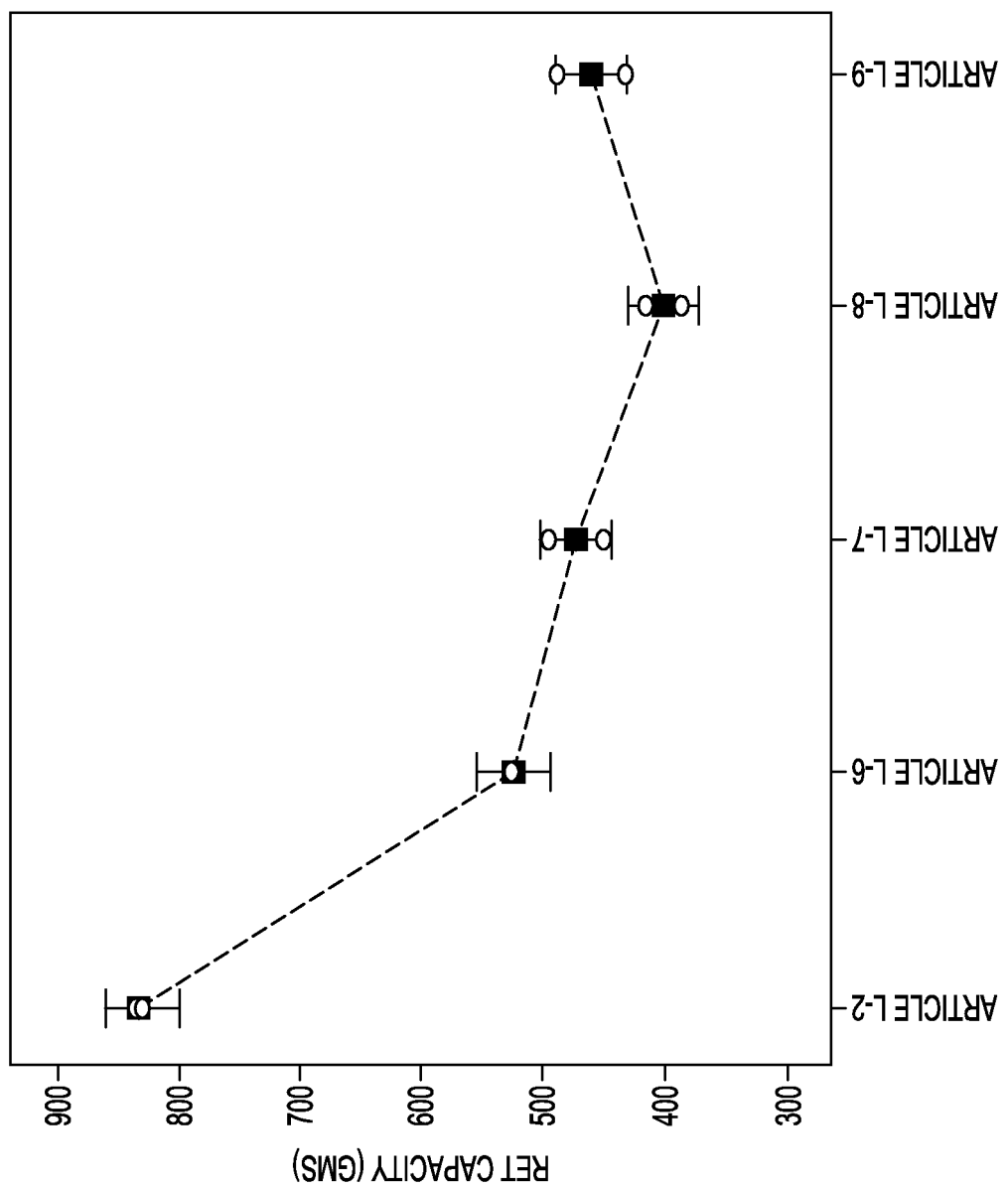
FIG. 15 illustrates generally experimental results showing retention characteristics for central cross-section regions from multiple absorbent articles.

FIGS. 13, 14, and 15 illustrate generally weight, total absorbency, and retention test results, respectively, for a subset of the Large articles. As in the examples of FIGS. 5-12, the labels "Article L-χ" refer to respective mean characteristics of multiple, similarly-constructed articles of the same type (i.e., articles of the same size and of the same group, brand, or model). Article L-2 again refers to an article prepared using a tri-core absorbent assembly according to the present disclosure. In the examples of FIGS. 13-15, instead of performing the tests using an entire article as in the examples of FIGS. 5-12, a central 380 mm section of each article was cut (measured from a center of the absorbent core). For example, referring again to FIG. 3, Article L-2 in the examples of FIGS. 13-15 corresponds to a cross-section of the absorbent article that includes the top core 103, the middle core 102, and the bottom core 101, and $L_{SECTION}$ is 380 mm.

FIG. 22 illustrates generally that a dry weight of Article L-2, such as prepared with a tri-core absorbent assembly according to the present disclosure, is on average greater than the other Large size articles under test. That is, Article L-2 includes a central portion, such as including the insult zone 300 of FIG. 3, that is more massive than a similarly sized central portion in other high absorption articles.

FIG. 14 illustrates generally a mean total absorbency for Article L-2 and Articles L-6 through L-9. FIG. 15 illustrates generally a mean retention capacity for Article L-2 and Articles L-6 through L-9. As shown, the cross-section of Article L-2, including the tri-core absorbent assembly according to the present disclosure, is characterized by a total absorbency that is greater than any of Articles L-6 through L-9 by several hundred grams. Under load, Article L-2 outperforms most of the other articles by about 35% or more.

Other features of the articles under test can be further discerned based on the examples of FIGS. 14 and 15. For example, Articles L-6 and L-7 likely have a similar first construction, and Articles L-8 and L-9 likely have a similar second construction, and the first and second constructions are different. In FIG. 14, Articles L-8 and L-9 each have a relatively high total absorbency characteristic, however, Articles L-6 and L-7 have better retention under load as shown in FIG. 15. Because SAP-based products generally show better retention under load than fluff-based products, it can be discerned from the results in FIGS. 14 and 15 that Articles L-6 and L-7 each have a relatively high SAP concentration, and that Articles L-8 and L-9 each have a relatively greater amount of fluff. Article L-2, including a tri-core absorbent assembly according to the present disclosure, however, outperforms any of L-6, L-7, L-8, and L-9, at least with respect to total absorption and liquid retention under load. The relative improvement in performance is due at least in part to Article L-2's multiple core structures, with each core structure having a different geometry, and with different SAP-to-fluff ratios in one or more of the core structures. Further, in Article L-2, the core structures are precisely placed relative to an expected insult zone to better capture liquid exudates when the article is worn or used.

NOTES & EXAMPLES

Example 1 can include or use subject matter such as an apparatus, or a method of making an apparatus, such as can include or use a disposable absorbent article comprising a liquid-impervious backsheet; a body-side top sheet; and an absorbent core assembly positioned between the liquid-impervious backsheet and the body-side top sheet. In Example 1, the absorbent core assembly can include an insult zone corresponding to a body-side insult surface area of the absorbent core assembly, the body-side insult surface area being less than a total body-side surface area of the absorbent core assembly, and discrete top, middle, and bottom absorbent core structures that are at least partially overlapping at the insult zone. In Example 1, at least two of the absorbent core structures can have different body-side surface areas.

Example 2 can include, or can optionally be combined with the subject matter of Example 1, to optionally include the bottom absorbent core structure is an airlaid core structure.

Example 3 can include, or can optionally be combined with the subject matter of Example 2, to optionally include extents of the bottom absorbent core structure that correspond to and define extents of the insult zone of the absorbent core assembly.

Example 4 can include, or can optionally be combined with the subject matter of one or any combination of Examples 1 through 3 to optionally include the disposable absorbent article has a maximum length dimension and a maximum width direction, the maximum length dimension being greater than the maximum width direction, wherein the maximum length dimension of the article extends from at least a first end of the absorbent core assembly to at least an opposite second end of the absorbent core assembly, and wherein the insult zone has a second maximum length dimension that is at least about 60% of the maximum length dimension of the disposable absorbent article.

Example 5 can include, or can optionally be combined with the subject matter of one or any combination of Examples 1 through 4 to optionally include the disposable absorbent article having a first total article mass characteristic, wherein a cross-section of the disposable absorbent article that includes only the insult zone has a second total mass characteristic, wherein the second total mass characteristic is at least about 60% of the first total article mass characteristic.

Example 6 can include, or can optionally be combined with the subject matter of Example 5, to optionally include the second total mass characteristic is at least 65% of the first total article mass characteristic.

Example 7 can include, or can optionally be combined with the subject matter of one or any combination of Examples 1 through 6 to optionally include a first portion of the absorbent core assembly corresponds to the insult zone and provides a first potential liquid retention capacity per unit dry volume, and a second portion of the absorbent core assembly corresponds to a second zone, outside of the insult zone, and provides a lesser second potential liquid retention capacity per the same unit dry volume.

Example 8 can include, or can optionally be combined with the subject matter of one or any combination of Examples 1 through 7 to optionally include a super absorbent polymer material in at least one of the top, middle, and bottom absorbent core structures in the absorbent core assembly. In Example 8, a density, volume, or concentration of the super absorbent polymer material relative to other materials in the absorbent core assembly can be greater in the insult zone than in a second zone of the absorbent core assembly that is peripheral to the insult zone.

Example 9 can include, or can optionally be combined with the subject matter of one or any combination of Examples 1 through 8 to optionally include the insult zone corresponds to a portion of the absorbent core assembly that is configured to more quickly absorb liquid than a peripheral portion of the absorbent core assembly that is outside of the insult zone.

Example 10 can include, or can optionally be combined with the subject matter of one or any combination of Examples 1 through 9 to optionally include an acquisition-distribution layer (ADL) positioned between the top sheet and backsheet and the ADL having a body-side surface area that is less than the total surface area of the absorbent core assembly, and wherein the ADL at least partially overlaps the insult zone.

Example 11 can include, or can optionally be combined with the subject matter of Example 10, to optionally include the body-side surface area of the ADL is substantially the same as the body-side insult surface area of the absorbent core assembly.

Example 12 can include, or can optionally be combined with the subject matter of one or any combination of Examples 1 through 11 to optionally include at least two of the absorbent core structures have different compositions.

Example 13 can include, or can optionally be combined with the subject matter of Example 12, to optionally include the at least two of the absorbent core structures having different compositions includes a first absorbent core structure having a first ratio of fluff to super absorbent polymer, and a second absorbent core structure having a different second ratio of fluff to super absorbent polymer.

Example 14 can include, or can optionally be combined with the subject matter of Example 13, to optionally include the super absorbent polymers in the first and second absorbent core structures are structurally different polymers.

Example 15 can include, or can optionally be combined with the subject matter of one or any combination of Examples 1 through 14 to optionally include the insult zone corresponds to a body-side surface area of the top absorbent core structure.

Example 16 can include, or can optionally be combined with the subject matter of one or any combination of Examples 1 through 15 to optionally include a body-side surface area of the bottom absorbent core structure is greater than a body-side surface area of the top absorbent core structure, and less than a body-side surface area of the middle absorbent core structure.

Example 17 can include, or can optionally be combined with the subject matter of one or any combination of Examples 1 through 15 to optionally include a body-side surface area of the bottom absorbent core structure is less than the body-side surface areas of both of the top and middle absorbent core structures.

Example 18 can include, or can optionally be combined with the subject matter of one or any combination of Examples 1 through 17 to optionally include the top absorbent core structure has a first body-side area and a first composition, and the middle absorbent core structure has a different second body-side area and a different second composition, and the bottom absorbent core structure has a different third body-side area and a different third composition.

Example 19 can include or use subject matter such as an apparatus, or a method of making an apparatus, such as can include or use a disposable absorbent article for use by incontinent individuals, the article comprising a top absorbent core structure having a first body-side surface area and a first composition, a middle absorbent core structure having a second body-side surface area and a second composition, and a bottom absorbent core structure having a third body-side surface area and a third composition. In Example 19, the third body-side surface area of the bottom absorbent core structure is less than the second body-side surface area of the middle absorbent core structure.

Example 20 can include, or can optionally be combined with the subject matter of Example 19, to optionally include the first body-side surface area of the top absorbent core structure is less than the second body-side surface area of the middle absorbent core structure.

Example 21 can include, or can optionally be combined with the subject matter of one or any combination of Examples 19 and 20 to optionally include the top absorbent core structure is substantially oval-shaped.

Example 22 can include, or can optionally be combined with the subject matter of one or any combination of Examples 19 through 21 to optionally include the middle absorbent core structure is substantially hourglass-shaped.

Example 23 can include, or can optionally be combined with the subject matter of one or any combination of Examples 19 through 22 to optionally include the bottom absorbent core structure is substantially rectangular.

Example 24 can include, or can optionally be combined with the subject matter of one or any combination of Examples 19 through 23 to optionally include the third body-side surface area of the bottom absorbent core structure defines an insult area of the article and the third body-side surface area is greater than the first body-side surface area of the top absorbent core structure.

Example 25 can include, or can optionally be combined with the subject matter of Example 24, to optionally include the bottom absorbent core structure has a higher SAP density or concentration per unit volume of the core structure than either of the top or middle absorbent core structures.

Example 26 can include, or can optionally be combined with the subject matter of one or any combination of Examples 24 and 25 to optionally include the insult area has an end-to-end length that is about 60% of an end-to-end length of the entire article.

Example 27 can include, or can optionally be combined with the subject matter of Example 26, to optionally include the article is a diaper, and wherein the insult area corresponds to a region between a wearer's legs when the diaper is worn.

Example 28 can include, or can optionally be combined with the subject matter of one or any combination of Examples 19 through 27 to optionally include the top, middle, and bottom absorbent core structures overlap in an expected insult area in the disposable article.

Example 29 can include, or can optionally be combined with the subject matter of Example 28, to optionally include a cross-section of the article, corresponding to the overlap, has at least about 60% of the mass of the entire article.

Example 30 can include, or can optionally be combined with the subject matter of Example 28, to optionally include a cross-section of the article, corresponding to the overlap, has a total absorbency characteristic that is at least about 65% of a total absorbency characteristic of the entire article.

Example 31 can include, or can optionally be combined with the subject matter of one or any combination of Examples 19 through 30 to optionally include the bottom absorbent core structure is an airlaid structure.

Example 32 can include, or can optionally be combined with the subject matter of one or any combination of Examples 19 through 31 to optionally include the first, second, and third compositions are each unique relative to the others.

Example 33 can include, or can optionally be combined with the subject matter of one or any combination of Examples 19 through 32 to optionally include the first and second compositions include respective different concentrations of fluff and super absorbent polymer (SAP) per unit volume of the respective structures.

Example 34 can include, or can optionally be combined with the subject matter of Example 33, to optionally include the first composition includes a combination of about two parts fluff to one part SAP by weight, and wherein the second composition includes a combination of about forty parts fluff to one part SAP by weight.

Example 35 can include or use subject matter such as an apparatus, or a method of making an apparatus, such as can include or use a method of making an absorbent article, the method comprising providing a top absorbent core structure having a first area and a first composition, providing a middle absorbent core structure having a second area and a second composition, wherein the second area is greater than the first area, providing a bottom absorbent core structure having a third area and a third composition, wherein the third area is less than the second area, and assembling an absorbent core assembly by layering the middle absorbent core structure over the bottom absorbent core structure, and by layering the top absorbent core structure over the middle absorbent core structure. In Example 35, the absorbent core assembly can include an insult zone where the top, middle, and bottom absorbent core structures overlap. In Example 35, the absorbent core assembly can provide a per-unit-volume absorption capacity in the insult zone that exceeds an absorption capacity of the absorbent core assembly outside of the insult zone.

Example 36 can include, or can optionally be combined with the subject matter of Example 35, to optionally include the providing the bottom absorbent core structure includes providing a structure having a first absorbency under load characteristic, and wherein at least one of the providing the top or middle absorbent core structures includes providing a structure having a lesser second absorbency under load characteristic.

Example 37 can include, or can optionally be combined with the subject matter of one or any combination of Examples 35 and 36 to optionally include the providing the bottom absorbent core structure includes providing an airlaid structure.

Example 38 can include, or can optionally be combined with the subject matter of one or any combination of Examples 35 through 37 to optionally include the providing the top absorbent core structure includes providing a structure having a length that is at most about 60% of a length of the middle absorbent core structure.

Example 39 can include, or can optionally be combined with the subject matter of one or any combination of Examples 35 through 38 to optionally include the providing the bottom absorbent core structure includes providing a structure having a length that is at most about 60% of a length of the middle absorbent core structure.

Each of these non-limiting examples can stand on its own, or can be combined in various permutations or combinations with one or more of the other examples in this document.

The above description is intended to be illustrative, and not restrictive. For example, the above-described examples (or one or more aspects thereof) may be used in combination with each other. Other embodiments can be used, such as by one of ordinary skill in the art upon reviewing the above description. In the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations.

The claimed invention is:

1. A disposable absorbent article comprising:
   a liquid-impervious backsheet;
   a body-side top sheet; and
   an absorbent core assembly positioned between the liquid-impervious backsheet and the body-side top sheet, the absorbent core assembly including:
   an insult zone corresponding to a body-side insult surface area of the absorbent core assembly, the body-side insult surface area being less than a total body-side surface area of the absorbent core assembly; and
   discrete top, middle, and bottom absorbent core structures that are at least partially overlapping at the insult zone, wherein the top, middle, and bottom absorbent core structures each comprise at least one of super absorbent polymer and fluff;
   wherein at least two of the absorbent core structures have different body-side surface areas;
   wherein a width of the bottom absorbent core structure is smaller than a width of the middle absorbent core structure; and
   wherein the bottom absorbent core structure has a lesser thickness than either of the top and middle absorbent core structures.

2. The article of claim 1, wherein the bottom absorbent core structure is an airlaid core structure, and wherein extents of the bottom absorbent core structure correspond to and define extents of the insult zone of the absorbent core assembly.

3. The article of claim 1, wherein the disposable absorbent article has a maximum length dimension and a maximum width direction, the maximum length dimension being greater than the maximum width direction;
   wherein the maximum length dimension of the article extends from at least a first end of the absorbent core assembly to at least an opposite second end of the absorbent core assembly; and
   wherein the insult zone has a second maximum length dimension that is at least 60% of the maximum length dimension of the disposable absorbent article.

4. The article of claim 1, wherein the disposable absorbent article has a first total article mass characteristic; and
   wherein a cross-section of the disposable absorbent article that includes only the insult zone has a second total mass characteristic, wherein the second total mass characteristic is at least 60% of the first total article mass characteristic.

5. The article of claim 1, wherein a first portion of the absorbent core assembly corresponds to the insult zone and provides a first potential liquid retention capacity per unit dry volume; and
   wherein a second portion of the absorbent core assembly corresponds to a second zone, outside of the insult zone, and provides a lesser second potential liquid retention capacity per the same unit dry volume.

6. The article of claim 1, comprising a super absorbent polymer material in at least one of the top, middle, and bottom absorbent core structures in the absorbent core assembly;
   wherein a density of the super absorbent polymer material relative to other materials in the absorbent core assembly is greater in the insult zone than in a second zone of the absorbent core assembly that is peripheral to the insult zone.

7. The article of claim 1, comprising an acquisition-distribution layer (ADL) positioned between the top sheet and backsheet and the ADL having a body-side surface area that is less than the total surface area of the absorbent core assembly, and wherein the ADL at least partially overlaps the insult zone.

8. The article of claim 1, wherein at least two of the absorbent core structures have different compositions, and wherein the at least two of the absorbent core structures having different compositions includes a first absorbent core structure having a first ratio of fluff to super absorbent polymer, and a second absorbent core structure having a different second ratio of fluff to super absorbent polymer.

9. The article of claim 8, wherein the super absorbent polymers in the first and second absorbent core structures are structurally different polymers.

10. The article of claim 1, wherein a body-side surface area of the bottom absorbent core structure is:
    greater than a body-side surface area of the top absorbent core structure, and
    less than a body-side surface area of the middle absorbent core structure.

11. The article of claim 1, wherein a body-side surface area of the bottom absorbent core structure is less than the body-side surface areas of both of the top and middle absorbent core structures.

12. The article of claim 1, wherein:
    the top absorbent core structure has a first body-side area and a first composition, and
    the middle absorbent core structure has a different second body-side area and a different second composition, and
    the bottom absorbent core structure has a different third body-side area and a different third composition.

13. The article of claim 1, wherein:
    the top absorbent core structure has a first body-side surface area and a first composition;
    the middle absorbent core structure has a second body-side surface area and a second composition; and
    the bottom absorbent core structure has a third body-side surface area and a third composition;
    wherein the third body-side surface area of the bottom absorbent core structure is less than the second body-side surface area of the middle absorbent core structure.

14. The article of claim 13, wherein the first body-side surface area of the top absorbent core structure is less than the second body-side surface area of the middle absorbent core structure.

15. The article of claim 13, wherein the third body-side surface area of the bottom absorbent core structure defines an insult area of the article and the third body-side surface area is greater than the first body-side surface area of the top absorbent core structure, and wherein the bottom absorbent core structure has a higher super absorbent polymer (SAP) concentration per unit volume of the core structure than either of the top or middle absorbent core structures.

16. The article of claim 13, wherein the top, middle, and bottom absorbent core structures overlap in an expected insult area in the disposable article, wherein a cross-section of the article, corresponding to the overlap, has at least 60% of the mass of the entire article, and wherein the cross-section of the article, corresponding to the overlap, has a total absorbency characteristic that is at least 65% of a total absorbency characteristic of the entire article.

17. The article of claim 13, wherein the first and second compositions include respective different concentrations of fluff and super absorbent polymer (SAP) per unit volume of the respective structures, and wherein the first composition includes a combination of about two parts fluff to one part SAP by weight, and wherein the second composition includes a combination of about forty parts fluff to one part SAP by weight.

18. A method of making an absorbent article, the method comprising:
provide a top absorbent core structure having a first area and a first composition;
providing a middle absorbent core structure having a second area and a second composition, wherein the second area is greater than the first area;
providing a bottom absorbent core structure having a third area and a third composition, wherein the third area is less than the second area; and
assembling an absorbent core assembly by layering the middle absorbent core structure over the bottom absorbent core structure, and by layering the top absorbent core structure over the middle absorbent core structure, wherein the top, middle, and bottom absorbent core structures each comprise at least one of super absorbent polymer (SAP) and fluff, and wherein a width of the bottom absorbent core structure is less than a width of the middle absorbent core structure;
wherein the absorbent core assembly includes an insult zone where the top, middle, and bottom absorbent core structures overlap; and
wherein the absorbent core assembly provides a per-unit-volume absorption capacity in the insult zone that exceeds an absorption capacity of the absorbent core assembly outside of the insult zone.

19. The method of claim 18, wherein the providing the bottom absorbent core structure includes providing a structure having a first absorbency under load characteristic, and wherein at least one of the providing the top or middle absorbent core structures includes providing a structure having a lesser second absorbency under load characteristic.

20. The method of claim 18, wherein the providing the top absorbent core structure includes providing a structure having a length that is at most 60% of a length of the middle absorbent core structure.

21. The method of claim 18, wherein the providing the bottom absorbent core structure includes providing a structure having a length that is at most 60% of a length of the middle absorbent core structure.

22. A disposable absorbent article comprising:
a liquid-impervious backsheet;
an acquisition-distribution layer (ADL);
a body-side top sheet; and
an absorbent core assembly, wherein the absorbent core assembly is positioned between the liquid-impervious backsheet and the ADL, and wherein the ADL is positioned between the absorbent core assembly and the body-side top sheet, the absorbent core assembly including:
an insult zone corresponding to a body-side insult surface area of the absorbent core assembly, the body-side insult surface area being less than a total body-side surface area of the absorbent core assembly; and
discrete top, middle, and bottom absorbent core structures that are at least partially overlapping at the insult zone, wherein the top, middle, and bottom absorbent core structures each comprise at least one of super absorbent polymer and fluff;
wherein at least two of the absorbent core structures have different body-side surface areas; and
wherein a length of the bottom absorbent core structure is at most 60% of a length of the middle absorbent core structure.

* * * * *